(12) United States Patent
Cipolla et al.

(10) Patent No.: US 7,572,124 B2
(45) Date of Patent: Aug. 11, 2009

(54) APPARATUS FOR SIMULTANEOUS ILLUMINATION OF TEETH

(75) Inventors: Anthony J. Cipolla, Trout Run, PA (US); John W. Warner, Warner, NH (US); Michael A. Williams, Midvale, UT (US)

(73) Assignee: Discus Dental, LLC, Culver City, CA (US)

(*) Notice: Subject to any disclaimer, the term of this patent is extended or adjusted under 35 U.S.C. 154(b) by 168 days.

(21) Appl. No.: 10/958,058

(22) Filed: Oct. 4, 2004

(65) Prior Publication Data

US 2005/0048434 A1   Mar. 3, 2005

Related U.S. Application Data

(60) Division of application No. 09/641,646, filed on Aug. 18, 2000, now abandoned, and a continuation-in-part of application No. 09/233,793, filed on Jan. 19, 1999, now Pat. No. 6,416,319.

(60) Provisional application No. 60/158,499, filed on Oct. 8, 1999, provisional application No. 60/075,222, filed on Feb. 19, 1998, provisional application No. 60/074,708, filed on Feb. 13, 1998.

(51) Int. Cl.
*A61C 3/00* (2006.01)
(52) U.S. Cl. ....................................................... 433/29
(58) Field of Classification Search .................. 433/29, 433/215, 91; 378/168–170
See application file for complete search history.

(56) References Cited

U.S. PATENT DOCUMENTS

| | | | |
|---|---|---|---|
| 3,544,220 A | 12/1970 | Kaye | 356/616 |
| 3,636,633 A | 1/1972 | Fuller et al. | 433/29 |
| 4,661,070 A | 4/1987 | Friedman | 433/203.1 |
| 4,790,752 A | 12/1988 | Cheslak | 433/37 |
| 4,802,851 A | 2/1989 | Rhoades | 433/93 |
| 4,952,143 A | 8/1990 | Becker et al. | 433/32 |

(Continued)

FOREIGN PATENT DOCUMENTS

EP          0950383          10/1999

(Continued)

OTHER PUBLICATIONS

International Preliminary Examination Report, PCT/US00/27643, Jun. 24, 2002.

(Continued)

*Primary Examiner*—John J Wilson

(57) ABSTRACT

An arrangement, for use in whitening a patient's teeth includes an arched surface and an array of light-generating devices, for example, light emitting diodes positioned on the arched surface. The light-generating devices are arranged to form a relatively uniform field of light in a particular range of wavelengths, and further arranged to focus the generated light in an overlapping manner onto a patient's teeth when the mouthpiece is properly positioned relative to the patient's face. The proper positioning is aided by a number of light sources, in the visible range, that shine on the patient's face in a predetermined manner when the mouthpiece is properly positioned. To remove whatever heat is generated at the surface of the patient's teeth in the course of the procedure, the mouthpiece includes air passages between the light emitting devices, and a fan that draws air away from the patient's face.

19 Claims, 16 Drawing Sheets

U.S. PATENT DOCUMENTS

| | | | | |
|---|---|---|---|---|
| 4,983,381 | A | | 1/1991 | Torres Zaragoza ............ 433/39 |
| 4,983,881 | A | | 1/1991 | Eliasson et al. ............. 313/607 |
| 5,032,178 | A | | 7/1991 | Cornell ........................ 106/35 |
| 5,240,415 | A | | 8/1993 | Haynie ....................... 433/216 |
| 5,316,473 | A | | 5/1994 | Hare ........................... 433/29 |
| 5,487,662 | A | | 1/1996 | Kipke et al. .................. 433/37 |
| 5,616,141 | A | | 4/1997 | Cipolla ........................ 433/29 |
| 5,634,711 | A | | 6/1997 | Kennedy et al. ............. 433/29 |
| 5,645,428 | A | | 7/1997 | Yarborough ................ 433/215 |
| 5,702,251 | A | | 12/1997 | McClintock, II ............ 433/80 |
| 5,738,519 | A | * | 4/1998 | Tenniswood ................. 433/92 |
| 5,785,527 | A | | 7/1998 | Jensen et al. ................ 433/215 |
| 5,785,703 | A | * | 7/1998 | Goodman et al. ............. 606/10 |
| 5,800,165 | A | | 9/1998 | Kirsch et al. .................. 433/29 |
| 5,813,854 | A | | 9/1998 | Nikodem ..................... 433/29 |
| D399,961 | S | | 10/1998 | Nikodem ................... D24/180 |
| D399,962 | S | | 10/1998 | Nikodem ................... D24/180 |
| 5,858,332 | A | | 1/1999 | Jensen et al. .................. 424/53 |
| 5,879,159 | A | | 3/1999 | Cipolla ........................ 433/29 |
| 6,038,287 | A | * | 3/2000 | Miles ......................... 378/117 |
| 6,077,073 | A | | 6/2000 | Jacob .......................... 433/29 |
| 6,102,696 | A | | 8/2000 | Osterwalder et al. .......... 433/29 |
| 6,162,055 | A | | 12/2000 | Montgomery et al. ....... 433/216 |
| 6,343,933 | B1 | | 2/2002 | Montgomery et al. ....... 433/216 |
| 6,416,319 | B1 | | 7/2002 | Cipolla ........................ 433/29 |
| 6,439,888 | B1 | * | 8/2002 | Boutoussov et al. ........ 433/215 |
| 2002/0172919 | A1 | * | 11/2002 | Zavitsanos et al. ............ 433/32 |

FOREIGN PATENT DOCUMENTS

| | | |
|---|---|---|
| FR | 2645734 | 10/1990 |
| WO | WO9937236 | 7/1999 |
| WO | WO9940870 | 8/1999 |

OTHER PUBLICATIONS

Discus Dental Inc.'s Answer to Second Amended Complaint; Counterclaim; and Demand for Jury Trial, Aug. 1, 2003, *BriteSmile* v. *Discus Dental*, Case No. C02-03220 JSW (N.D. Calif.).

Defendant Discus Dental, Inc.'s Preliminary Invalidity Contentions, with Exhibit B thereto, Sep. 29, 2003, *BriteSmile* v. *Discus Dental*, Case No. C02-03220 JSW (N.D. Calif.).

Production of Documents Accompanying Defendant Discus Dental, Inc.'s Preliminary Invalidity Contentions, Sep. 29, 2003, *BriteSmile* v. *Discus Dental*, Case No. C02-03220 JSW (N.D. Calif.).

Jandt et al., "Depth of Cure and Compressive Strength of Dental Composites Cured With Blue Light Emitting Diodes (LEDs)," Dental Materials, 16 (2000) 41-47.

Stahl et al., "Light-Emitting Diode (LED) Polymerisation of Dental Composites: Flexural Properties and Polymerization Potential," Biomaterials, 21 (2000) 1379-1385.

"Renamel Hybrid For Class 2 Restorations," Clinical Research Associates Newsletter, vol. 24, Issue 8, pp. 1-4 (Aug. 2000).

Operating Instructions: Illuminator, The Union Broach Bleaching System (1978).

* cited by examiner

TO REMAINDER OF ARM

APPARATUS FOR SIMULTANEOUS ILLUMINATION OF TEETH

CROSS REFERENCE TO RELATED APPLICATIONS

This application is a division of U.S. patent application Ser. No. 09/641,646, filed Aug. 18, 2000 now abandoned, which claims benefit of U.S. provisional application No. 60/158,499, filed Oct. 8, 1999, and which in turn is a continuation-in-part of U.S. patent application Ser. No. 09/233,793, filed Jan. 19, 1999, now U.S. Pat. No. 6,416,319, which claims benefit of U.S. provisional application No. 60/074,708, filed Feb. 13, 1998, and U.S. provisional application No. 60/075,222, filed Feb. 19, 1998. All of the foregoing applications are hereby incorporated by reference to the fullest extent permitted by law.

FIELD OF THE INVENTION

The present invention relates to the field of cosmetically improving and altering the appearance of teeth, and more particularly, to apparatus that is employed in light-activated bleaching of teeth.

BACKGROUND OF INVENTION

White teeth have long been considered cosmetically desirable. Unfortunately, due to the presence of chromogenic (color-causing) substances in food, beverages, tobacco, and salivary fluid, in addition to internal sources such as blood, amalgam restoratives, and antibiotics such as tetracycline, teeth become almost invariably discolored in the absence of intervention. The tooth structures that are generally responsible for presenting a stained appearance are enamel, dentin, and the acquired pellicle. Tooth enamel is predominantly formed from inorganic material, mostly in the form of hydroxyapatite crystals, and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer on the surface of tooth enamel which reforms rapidly after an intensive tooth cleaning.

A tooth stain classification system, termed the N (Nathoo) Classification System, has been proposed (J. of the Amer. Dental Asso., Vol. 128, Special Supplement, April 1997). One form of direct dental stain is the N1 type stain which occurs when a chromogenic material binds to the tooth surface to cause discoloration similar in color to that of the unbound chromogen. Another type of direct dental stain is the N2 type stain, in which a chromogenic material binds to the toothsurface and subsequently undergoes a color change after binding to the tooth. Finally, an N3 stain is an indirect dental stain, caused by the binding of a colorless material (prechromogen) to the tooth, said prechromogen undergoing a chemical reaction that converts it into a chromogen that causes tooth stain. Tooth stains may be either extrinsic or intrinsic, depending upon their location within the tooth structure. For example, extrinsic staining of the acquired pellicle arises as a result of compounds such as tannins and other polyphenolic compounds which become trapped in and tightly bound to the proteinaceous layer on the surface of the teeth. This type of staining can usually be removed by mechanical methods of tooth cleaning that remove all or part of the acquired pellicle together with the associated stain. In contrast, intrinsic staining occurs when chromogens or prechromogens penetrate the enamel and dentin and become tightly bound to the tooth structure. Intrinsic staining may also arise from systemic sources of chromogens or prechromogens, for instance, when excess fluoride intake during enamel development leads to the mottled yellow or brown spots typical of fluorosis staining. Intrinsic staining is not amenable to mechanical methods of tooth cleaning and generally requires the use of chemicals, such as hydrogen peroxide, that can penetrate into the tooth structure, in order to affect a change in the light absorptivity of the chromogen. Intrinsic tooth staining is generally more intractable and difficult to remove than extrinsic tooth staining.

Consequently, tooth-bleaching compositions generally fall into two categories: (1) gels, pastes, or liquids, including toothpastes that are mechanically agitated at the stained tooth surface in order to affect tooth stain removal through abrasive erosion of stained acquired pellicle; and (2) gels, pastes, or liquids that accomplish the tooth-bleaching effect by a chemical process while in contact with the stained tooth surface for a specified period, after which the formulation is removed. In some cases, an auxiliary chemical process or additive, which may be oxidative or enzymatic, supplements the mechanical process.

Among the chemical strategies available for removing or destroying tooth stains, the most effective compositions contain an oxidizing agent, such as hydrogen peroxide, in order to attack the chromogen molecules in such a way as to render them colorless, water-soluble, or both. In one of the most popular approaches to whitening a patient's teeth, a dental professional will construct a custom-made tooth-bleaching tray for the patient from an impression made of the patient's dentition and prescribe the use of an oxidizing gel to be dispensed into the tooth-bleaching tray and worn intermittently over a period of time ranging from about 2 weeks to about 6 months, depending upon the severity of tooth staining. These oxidizing compositions, usually packaged in small plastic syringes, are dispensed directly by the patient, into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition. The most commonly used oxidative compositions contain the hydrogen peroxide precursor carbamide peroxide which is mixed with an anhydrous or low-water content, hygroscopic viscous carrier containing glycerin and/or propylene glycol and/or polyethylene glycol. When contacted by water, carbamide peroxide dissociates into urea and hydrogen peroxide. Associated with the slow rate of bleaching in the hygroscopic carrier, the currently available tooth-bleaching compositions cause tooth sensitization in over 50% of patients. Tooth sensitivity is believed to result from the movement of fluid through the dentinal tubules, which is sensed by nerve endings in the tooth. The carriers for the carbamide peroxide enhance this movement. In fact, it has been determined that glycerin, propylene glycol and polyethylene glycol can each give rise to varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These include: solubilization of calcium from the enamel layer at a pH less than 5.5 with associated demineralization; penetration of the intact enamel and dentin by the bleaching agents, so as to reach the pulp chamber of a vital tooth thereby risking damage to pulpal tissue; and dilution of the bleaching compositions with saliva resulting in leaching from the dental tray and subsequent ingestion.

Alternatively, there are oxidizing compositions (generally those with relatively high concentrations of oxidizers) which are applied directly to the tooth surface of a patient in a dental office setting under the supervision of a dentist or dental hygienist. Theoretically, such tooth whitening strategies have the advantage of yielding faster results and better overall patient satisfaction; however, due to the high concentration of oxidizing agents contained in these so called "in-office" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), through which only the teeth protrude. Alternatively, the soft tissue may be isolated from the oxidizers to be used in the whitening process by covering said soft tissue with a polymerizable composition that is shaped to conform to the gingival contours and subsequently cured by exposure to a high intensity light source. Once the soft tissue has been isolated and protected, the practitioner may apply the oxidizing agent directly onto the stained tooth surfaces for a specified period of time or until a sufficient change in tooth color has occurred. Typical results obtained through the use of a in-office tooth whitener, with or without activation by heat, range from about 2 to 3 shades (as measured with the VITA® Shade Guide, VITA® Zahnfarbik, Bad Sackingen, Germany).

The range of tooth shades in the VITA® Shade Guide varies from very light (B1) to very dark (C4). A total of 16 tooth shades constitute the entire range of colors between these two endpoints on a scale of brightness. Patient satisfaction with a tooth whitening procedure increases with the number of tooth shade changes achieved. Typically, the minimum generally accepted change is about 4 to 5 VITA® shades.

Attempts have been made to activate peroxides with heat and/or light for the purpose of whitening teeth. U.S. Pat. No. 4,661,070 discloses a method of whitening stained teeth which includes the application of a concentrated solution of hydrogen peroxide within the pulp chamber or upon the surface of a discolored tooth, followed by exposing the discolored tooth to optical energy consisting of both ultraviolet and infrared light. The preferred wavelengths of light disclosed by this patent are from 320 to 420 nanometers and from 700 to 1200 nanometers, with light in the visible spectrum (wavelengths from 500 and 700 nanometers) being suppressed. The disclosed method suffers from two serious drawbacks: (1) ultraviolet light can be hazardous to the patient and practitioner alike and (2) infrared light may cause irreversible pulpitis if not handled with care.

These drawbacks are partially addressed in U.S. Pat. No. 4,952,143 which discloses a dental bleaching instrument which filters out ultraviolet light and has a temperature regulation mechanism. This patent also discloses the use of visible light with wavelengths ranging from 450 to 500 and 650 to 750 nanometers to produce a dark reddish/purple beam which facilitates the aiming and focusing of the instrument.

U.S. Pat. No. 5,032,178 discloses compositions and methods to improved tooth whitening efficacy which uses exposure to "optical energy", preferably in the visible spectrum wavelength range of 400 to 700 nanometers. The compositions disclosed in this patent require the use of (1) an inert silica gelling agent, (2) a catalytic accelerator (either manganese sulfate monohydrate or ferrous sulfate), (3) an agent for providing thixoplasticity and thickening properties to the composition, such as cellulose ethers and methyl vinyl ethers, and (4) a means for indicating completion of the bleaching treatment of the teeth, comprising a redox color indicator for transforming from one color to another in response to the dissociation of hydrogen peroxide over a given time period. Compositions described therein are mixed homogeneously prior to use and all of the required components, including the catalyst, are dispersed evenly throughout the mixture. The compositions described are not highly transparent to light energy in the range of 400 to 700 nm, due to the presence of the high levels of inorganic silica particles. Commercial mixtures based on this patent (available under the trade name Shofu Hi-Lite® from Shofu Dental Corporation, Menlo Park, Calif.) confirm that these preparations are not transparent to visible light, but rather are quite opaque. Typical results obtained using such compositions and methods are about 2 to 3 VITA® shades improvement in tooth color, similar to that achieved with compositions that do not employ light energy in the process of bleaching teeth.

U.S. Pat. No. 5,240,415 discloses a dental bleaching system comprising a multi-component kit, one of the required components of said kit being fumed silica. As described above, silica renders an aqueous composition relatively opaque to visible light energy. Again, a tooth shade improvement of about 2 to 3 VITA® shades can be expected through the use of this type of composition.

A commercial product called Opalescence Xtra available for bleaching teeth in the controlled environment of a dental office has recently been introduced by Ultradent Products, Inc, South Jordan, Utah. This product is believed to be based on the disclosure of U.S. Pat. No. 5,785,527. The commercial product is supplied in a plastic syringe and is described in the accompanying literature as a light-activated tooth whitening gel, which contains approximately 35% hydrogen peroxide. A pH determination showed the product to have a neat pH at 25° C. of about 4.0. The product is thickened to a loose, gel-like consistency with a polymer. Additionally, the product as sold, and as disclosed in U.S. Pat. No. 5,785,527, contains a bright orange pigment or dye (carotene), which presumably serves as the "photosensitizer". The manufacturer also claims that the photosensitizer is able to absorb light energy and convert it into heat energy, thereby increasing the activity of the peroxide as a tooth bleaching agent. The presence of a photoabsorber in the aforementioned composition renders it relatively opaque to wavelengths from about 400 to 700 nm. Exposure of this composition to light energy between 400 and 700 nm results in a gradual fading of the orange color, presumably due to a photobleaching effect in the presence of the hydrogen peroxide. Comparative clinical results show an improvement in tooth color of from about 3 to 4 VITA® shades, which is highly dependent upon the contact time of the composition on the tooth surface, rather than any particular light or heat activation regimen. In addition, the low pH of the commercial product may cause a reduction in the microhardness of tooth enamel, due to the dissolution of hydroxyapatite crystals (which can occur at a pH of around 5.5 or less).

Devices for use in light/heat-activated tooth whitening procedures include the commercially available Union Broach Illuminator System, from Union Broach, a Health\Chem Company, New York, N.Y. This device, as described by the manufacturer, provides direct, full spectrum illumination to all of the teeth found in the front of the average adult's mouth. However, this device does not uniformly illuminate all sixteen central teeth in the front upper and lower arches because of the curvature of the dentition. This potentially gives rise to uneven results. In addition, the Union Broach device generates a great deal of heat which is both uncomfortable for the patient and potentially damaging to the teeth.

There is thus a need for improved compositions, methods and devices for whitening teeth that overcome the limitations of the prior art described above. In particular, there is a need for tooth whitening compositions and methods capable of whitening teeth quickly and safely, without harm to tooth enamel, dentin, or pulp. The compositions and methods of the present invention described herein satisfy these and other needs.

It is an object of this invention to provide fast and safe tooth whitening compositions and methods that can be activated or accelerated by the use of light energy.

It is a further object of this invention to provide a tooth whitening composition that shortens the treatment time required to obtain a given level of tooth whitening that is satisfactory to both the patient and the dentist.

It is another object of the present invention to provide tooth whitening compositions that are relatively transparent to light energy in the wavelength range at which tooth chromogens absorb in order to allow exposure of the tooth enamel surface to said light energy while in contact with said tooth whitening compositions.

SUMMARY OF THE INVENTION

The present invention encompasses methods for whitening teeth, wherein a stained tooth surface is contacted with (i) a tooth whitening composition that is transparent to photoactive light and (ii) a photosensitive agent that is responsive to the wavelengths of light that are transmitted through the whitening composition and, after contacting with the composition and agent, the tooth is exposed to a biologically safe and effective level of photoactinic light in order to enhance the ability of the oxidizing compound in the whitening composition to effect rapid tooth whitening.

Also disclosed and contemplated within the scope of this invention are methods for whitening teeth, wherein a stained tooth surface is contacted with an oxidizing compound that is transparent to the wavelengths of light that are absorbed by tooth stain chromogens, and then exposing the treated tooth to a biologically safe and effective level of those same wavelengths of light in order to effect rapid tooth whitening.

Also disclosed and contemplated within the scope of this invention are the compositions and compounds described above and devices for whitening teeth, wherein a minimum of eight central teeth in both the upper and lower arches in an adult are simultaneously and uniformly illuminated with a biologically safe and effective level of actinic light to effect rapid tooth whitening.

An improvement in the art is achieved with an arrangement where a tooth whitening composition is applied to a patient's teeth and where a mouthpiece that is placed in a position outside of a patient' mouth includes means for generating a light that is adapted to be simultaneously applied to all of the patient's teeth and to, thereby, accelerate the tooth whitening process.

In one embodiment, a mouthpiece having an arched surface not unlike the arched surface of prior art mouthpieces includes an array of light-generating devices, for example, light emitting diodes. The light-generating devices are arranged to form a relatively uniform field of light in a particular range of wavelengths, and further arranged to generally concentrate the generated light onto a patient's teeth when the mouthpiece is properly positioned relative to the patient's occlusal plane. In one embodiment, the proper positioning is aided by a number of light sources, in the visible range, that shine on the patient's face in a predetermined manner when the mouthpiece is properly positioned. In another embodiment, the mouthpiece is aligned with a positioning device that is held between the patient's teeth (i.e., in the occlusal plane). To remove whatever heat is generated in the mouthpiece unit in the course of the procedure, the mouthpiece includes air passages, and a fan that draws air through the mouthpiece and away from the patient's face.

DETAILED DESCRIPTION OF THE PREFERRED EMBODIMENTS

Figure 1:
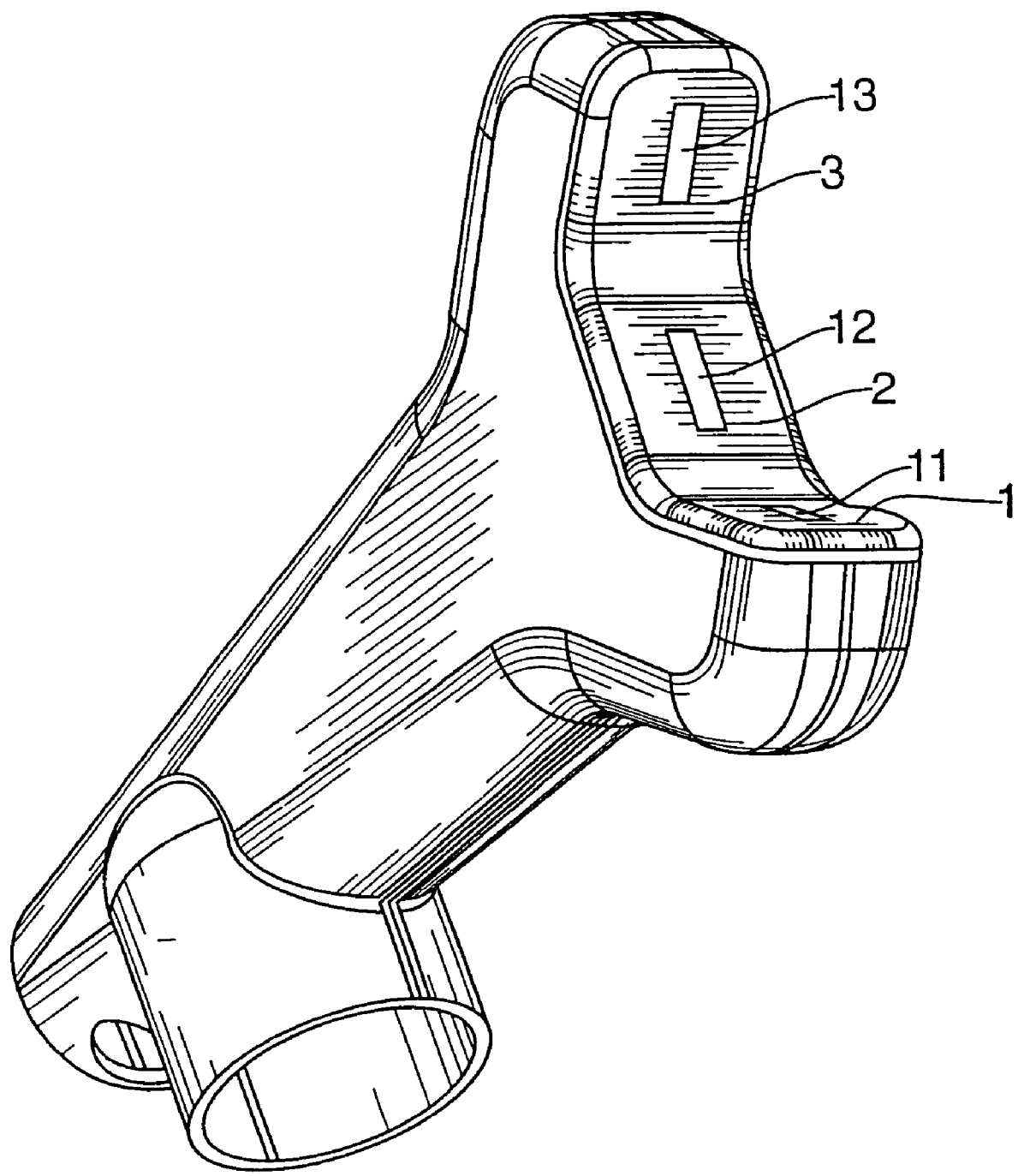
FIG. 1: A diagram of a device for illuminating the eight central teeth in both the upper and lower arches of an adult for use in a light-activated tooth whitening procedure.

This section details the preferred embodiments of the subject invention. These embodiments are set forth to illustrate the invention, but are not to be construed as limiting. Since the present disclosure is directed to those skilled in the art field and is not primer on the manufacture of tooth whitening compositions or their use or on devices for using such compositions, basic concepts and standard features known to those skilled in the art are not set forth in detail. Details for concepts such as choosing appropriate construction materials or ingredients, operating conditions or manufacturing techniques, etc. are known or readily determinable to those skilled in the art. Attention is directed to the appropriate texts and references known to those skilled in the art for details regarding these and other concepts which may be required in the practice of the invention; see, for example, Kirk-Othmer Encyclopedia of Chemical Technology, 4th Edition, Volumes 4 (1992), 13 (1995), 18 (1996), John Wiley & Sons, NY; Goldstein and Garber, *Complete Dental Bleaching*, Quintessence Publishing Co. 1995; and the aforementioned Journal of the American Dental Association, Vol. 128, Special Supplement, April 1997, the disclosures of which are hereby incorporated by reference into the present disclosure to aid in the practice of the invention. The development of the inventive compositions and methods described herein resulted from the unexpected discovery that extremely rapid tooth whitening occurs by allowing actinic radiation to penetrate through the oxidizing compound, which is placed directly onto the tooth surface to be whitened. This discovery is antithetical to all prior art compositions that include a light (or heat) absorbing additive dispersed directly in and homogeneously throughout the oxidizing compound. The inventive compositions, on the other hand, allow actinic radiation to reach the stained tooth surface at higher power densities than prior art compositions that are specifically designed to absorb light. Actinic radiation is thus more effectively utilized compared to prior art compositions and methods in which compositions are both opaque to most wavelengths of light and are activated directly by the actinic radiation. As the greatest oxidizing activity is required in the few millimeters of enamel and dentin at the tooth surface, the present inventive compositions and methods are more effective at removing tooth stains, in many cases with lower levels of active oxidizing agents, thereby resulting in safer compositions for use in the oral cavity.

For the purpose of this disclosure, the term actinic radiation shall mean light energy capable of being absorbed by either an exogenous photosensitizing agent or an indigenous tooth chromogen. Also for the purpose of this disclosure, photosensitizing actinic radiation will mean light absorbed by a specific photosensitive agent, where as chromosensitizing actinic radiation will mean light absorbed by one or more tooth chromogens. The terms "actinic radiation" and "actinic light" will be referred to interchangeably.

Also for the purposes of this disclosure, the term "transparent" shall mean having greater than 70% transmission of light at a specified wavelength or within a wavelength range. In addition, all composition ingredient percentages are by weight unless otherwise stated.

Various modes of application of the inventive tooth bleaching compositions are effective, although methods that allow for the accumulation or concentration of the photosensitizer within the acquired pellicle, enamel, and dentin (the three tooth structure primarily associated with the majority of tooth staining) are most preferred. This is best accomplished by contacting the stained tooth surface with the photosensitizer prior to contacting the same stained tooth surface with the oxidizing composition. In this way, the photosensitizer is able to penetrate into the tooth structure, thus being present at the site of the tooth chromogen(s) prior to contact with the oxidizing composition and prior to exposure to the actinic radiation source.

Photosensitizing agents useful in accomplishing the desired tooth whitening effect include any compounds capable of absorbing light energy at biologically acceptable wavelengths prescribed by the limits of safety for use in the oral cavity. In general, such wavelengths are from about 350 nanometers (nm) to about 700 nm, encompassing a portion of the UVA spectrum (300 to 400 nm) and most of the visible light spectrum (400 to 700 nm). Examples of compounds which may convert light energy to either heat of chemical energy, include semiconductor particles (particularly nanometer-scale titanium dioxide and zinc oxide), benzophenone derivatives, benzotriazole derivatives, diketones (such as camphorquinone and benzil), metal-ligand complexes (such as ferric potassium oxalate, manganese gluconate, and various metal—bisphosphonate chelates), phthalocyanin-metal complexes, and others. A specific example of a suitable photosensitizing composition is an aqueous dispersion of zinc oxide with particle sizes between 5 and 20 nanometers. Any molecule capable of absorbing a photon of light in the wavelength range of from about 350 nm to about 700 nm and subsequently converting the energy in said photon of light into the useful energy of oxidation either alone or in the presence of an auxilliary oxidizing agent, is contemplated to have utility in the practice of the present invention.

It is preferred that the inventive photosensitizers are of a molecular size, charge, pH and hydrophobicity/hydrophilicity to allow for effective penetration into the deeper structures of enamel and dentin. The more readily a photosensitizer penetrates the tooth structure, the more likely that, upon exposure of the photosensitizer to actinic radiation at the appropriate wavelength and energy, said energy will be converted into oxidative activity at the site of, or in close proximity to, the chromogen itself. Photosensitizers having a molecular size, net charge, pH, and/or a hydrophobicity/hydrophilicity which prevent or limit penetration into deeper tooth structures are of utility in the practice of the present invention, but may be limited to the removal and/or destruction of chromogens located at the outer tooth surface (extrinsic stains).

Especially preferred photosensitizers belong to the general class of water-soluble metal-ligand complexes which absorb light in the range of from about 350 nm to about 700 nm. For the purposes of the present disclosure, the term "ligand" will mean an organic molecule capable of complexing or associating with a metal ion in aqueous solution, such that the reactivity, solubility, or any other physical property of said metal ion is changed. Such metal-ligand complexes are also known as metal-coordination complexes. Suitable metals ions include iron, manganese, copper, and other transition metal ions. Various valence states may be used or may be present simultaneously. The metal ions may be present in saliva, plaque, or the acquired pellicle on the tooth surface. Metal ions may also contribute, through formation of oxides, to certain types of tooth stains. Suitable metal ion ligands include chelating agents capable of associating with the metal ions above in aqueous solution, resulting in a water-soluble metal-chelate complex that absorbs light between about 350 and 700 nm. Illustrative, but by no means limiting, examples of metal-coordination complexes are formed from the association of iron, manganese and copper with chelators such as ethylenediamine tetraacetic acid (EDTA), diethylenetriamine pentaacetic acid (DETPA), nitrilotriacetic acid (NTA), 1-hydroxyethylidene-1,1-diphosphonic acid, ethylenediamine tetra(methylenephosphonic acid), diethylenetriamine penta (methylenephosphonic acid), and polyols such as sorbitol, xylitol, mannitol, maltitol, lactitol and other non-carboxylated polyhydroxy compounds more fully described in EP 443,651, such description being incorporated herein by reference. Any organic multidentate chelating agent capable of forming a photoabsorbing coordination complex with a metal ion can be presumed to have utility in the present inventive compositions for and methods of whitening stained teeth.

A number of the inventive metal-ligand complexes have an absorption spectrum that is pH-dependent; in general, such complexes will display a greater degree of absorption between 350 and 700 nm at a pH of greater than about 4.0, light absorption in this range increasing with increasing pH. For instance, the aqueous complex formed between 1-hydroxyethylidene-1,1-diphosphonic acid and ferrous ions is virtually transparent to visible light at pH 3.0, but absorbs strongly in the spectral region between 350 and 500 nm as the pH is raised to 7.0.

In some cases, a photosensitizer precursor may be included directly within the oxidizing composition, where it does not readily absorb light in the visible region of the spectrum from 400 to 700 nm. However, upon contact with the tooth surface (when placed there with the oxidizing composition), the photosensitizer precursor may combine, for instance, with a metal ion such as iron present in saliva or found in the interstitial fluid of enamel and dentin, resulting in the formation, in situ, of an active photosensitizer capable of activating the oxidizing compound upon exposure to actinic radiation. Obviously, only those compounds that are stable in a highly oxidative environment are suitable for inclusion directly in the oxidizing composition. An example of such a compound is 1-hydroxyethylidene-1,1-diphosphonic acid (available commercially under the trade name Dequest 2010 and sold as a 60% active solution by Monsanto Corporation, St. Louis, Mo.).

The ability of certain metal chelates to act as photosensitizers has been noted in the literature by various workers. For example, Van der Zee, et al ("Hydroxyl Radical Generation by a Light-Dependent Fenton Reaction" in Free Radical Biology & Medicine, Vol. 14, pp 105-113, 1993) described the light-mediated conversion of Fe (III) to Fe (II) in the presence of a chelating agent and hydrogen peroxide. The reduction of Fe (III) chelates by light at 300 nanometers to yield Fe (II) was shown to proceed steadily over a period of about 30 minutes, with conversions to Fe (II) ranging from about 40% to about 80%, depending upon the particular chelating compound studied. The Fe (II) thus created initiated a Fenton-type degradation of the hydrogen peroxide, yielding hydroxyl radicals that were spin-trapped and detected by electron spin resonance (ESR). It was not suggested or implied by the authors that this photochemical reaction would have utility in the oxidation of chromophores, such as those found in a human tooth.

Useful oxidizing compounds include liquids and gels, preferably containing a peroxide or peroxyacid known in the art. Such oxidizing compounds include, but are not limited to, hydrogen peroxide, carbamide peroxide, alkali metal peroxides, alkali metal percarbonates, and alkali metal perborates. Often, it may be desirable to utilize a peroxyacid compound, such as peroxyacetic acid (for instance, when attempting to eliminate highly intractable tooth stains caused by tetracycline) in the tooth whitening composition. The peroxyacid may be included directly within the oxidizing composition (providing that transparency to light energy between about 350 and about 700 nanometers is maintained). Alternatively, the peroxyacid may be formed by combining two or more separate phases (one of which contains a peroxyacid precursor, such as glyceryl triacetate and a second that contains one of the oxidizing compounds listed above) prior to application to the tooth surface. Preferably, the peroxyacid is formed in situ, by contacting the tooth surface with a peroxyacid precursor prior to the application of an oxidizing compound; the peroxyacid is thus formed only on and within the stained tooth structure, where it is most beneficial to the tooth whitening process. Suitable peroxyacid precursors include, but are not limited to, glyceryl triacetate, acetylated amino acids, acetylsalicylic acid, and N,N,N',N'-tetraacetyl ethylenediamine, vinyl acetate polymers and copolymers, acetylcholine, and other biologically acceptable acetylated compounds.

The oxidizing compounds are liquid, gel, or solid compositions transparent to the wavelength(s) of light capable of activating the photosensitizing agent at the tooth surface; light energy otherwise will be attenuated by the film or layer of oxidizing compound between the actinic radiation source and the photosensitizer at the tooth enamel surface. As the tooth enamel surface is the location of the tooth discoloration, the most effective method of whitening teeth will occur when most or all of the light energy reaches the photosensitizer at the tooth enamel surface. An example of a suitable composition that is transparent to light energy between 380 and 500 nm is a 6% hydrogen peroxide gel with a pH of about 7.0 that has been thickened to approximately 100,000 cps with neutralized carboxypolymethylene.

Another unexpected benefit of utilizing an oxidizing composition transparent to photosensitizing actinic radiation is that certain wavelengths of light seem to be absorbed by tooth chromogens in a manner that promotes their oxidation to a non-chromogenic state. Reflectance studies show that dentin and enamel transmit green light, reflect yellow/red light and absorb blue light. Although not wishing to be bound by any particular theory, light is absorbed by the molecules responsible for tooth discoloration; thus, tooth chromogens may act in a manner similar to that of photosensitizers. In particular, exposure to certain wavelengths may raise the energy state level of pi electrons carbonyl ($C=O$), double bond ($C=C$) and conjugated double bond ($C=C-C=C$) moieties, making them more susceptible to attack by active oxidizing species such as perhydroxyl anion (HOO—), peroxyacid anions (RCOOO—), and radical species such as hydroxyl radical (HO*) and perhydroxyl radical (HOO*). In order to destroy or solubilize chromogenic substances, the activation energy of the reaction between one of the above light-absorbing moieties and an active oxidizing species must be overcome; thus, light assisted chromogen attack leads to more efficient destruction of the molecular moieties responsible for the appearance of tooth discoloration by raising the energy state of electrons in specific chemical bonds within a light-absorbing molecule from a normal pi bonding orbital to a pi anti-bonding orbital. Whilst in the less stable pi antibonding orbital, a light absorbing double bond has considerable single bond character and is much more easily attacked by oxidizing agents such as peroxides and peroxyacids. In theory, actinic light of a specific energy and wavelength, simply through the process described above, may utilize a tooth chromogen molecule as a photosensitizer in order to improve the efficacy of a given oxidative composition in contact with said tooth chromogen.

A light-activated tooth whitening method, in accordance with a specific embodiment of the invention includes contacting the tooth enamel surface with the photosensitizing agent, then contacting the photosensitizer-treated tooth surface with the oxidizing compound, and, thereafter, exposing the tooth surface to light energy capable of activating the photosensitizer which, in turn, activates the oxidizing compounds at the tooth enamel surface.

Another light-activated tooth whitening method, in accordance with another embodiment of the invention includes contacting the tooth enamel surface with an oxidizing compound which contains a photosensitizer precursor, whereby said precursor is seen to absorb actinic radiation in the range of 350 to 700 nm only after contact with said tooth surface. Once the photosensitizer precursor becomes light absorbent, the tooth surface is exposed to light energy capable of activating the now absorbent photosensitizer, which in turn activates the oxidizing compound at the tooth surface to whiten the tooth.

A further light-activated tooth whitening method, in accordance with another embodiment of the invention includes contacting the tooth enamel surface with an oxidizing compound and thereafter exposing said tooth enamel surface to actinic radiation corresponding to a tooth chromogen molecule absorption wavelength. The preferred wavelengths of light in this embodiment include those between about 350 and about 700 nanometers, a more preferred embodiment include those between about 380 and about 550 nanometers with the most preferred wavelengths being between about 400 and about 505 nanometers. As in all of the methods described above, the oxidizing composition must be transparent to the actinic radiation utilized in order to allow the wavelength-specific light energy to reach the tooth surface and underlying structure.

Yet another light-activated tooth whitening method, in accordance with another embodiment of the invention includes contacting the tooth enamel surface with a peroxyacid precursor prior to contacting said tooth enamel surface with an oxidizing compound and subsequently exposing to actinic radiation as described above. The peroxyacid precursor may be placed on the tooth surface together with or separately from a photosensitizer.

Stained teeth may be treated individually, for instance, by directing the light to a single tooth surface by means of a fiber optic light guide. In this manner, several stained teeth are exposed to light in sequence, the dentist or hygienist moving the light guide from tooth to tooth during the procedure. This process is both labor intensive and time consuming for the dentist or hygienist as well as tedious for the patient. Alternatively, all of the stained teeth may be exposed to light simultaneously either by direct illumination from a light source shaped substantially like the dental arch or by indirect illumination from a light guide or device that is capable of illuminating all of the front teeth at once.

One such device for the simultaneous and uniform illumination of at least eight central teeth in both the upper and lower arches is illustrated in FIG. 1. This preferred embodiment has three linear optical outputs 11, 12, and 13 precisely positioned on three front (patient facing) surfaces 1, 2, and 3. In a more preferred six bar embodiment, two three bar devices are stacked one on the other resulting in six optical outputs on the front patient facing surfaces as illustrated in FIG. 2.

Figure 2:
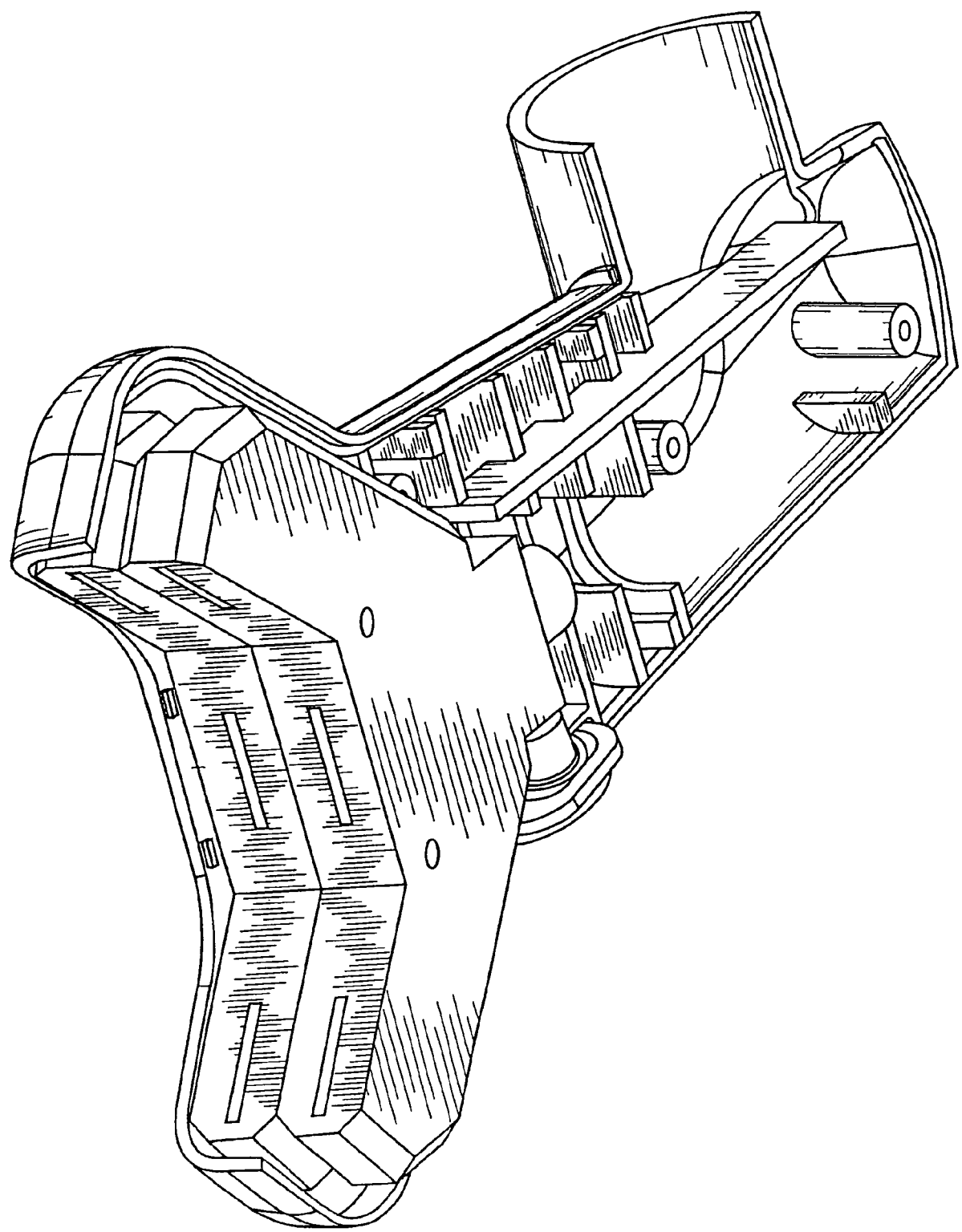
FIG. 2: A diagram illustrating the position of two devices for illuminating the eight central teeth in both the upper and lower arches of an adult for use in a light-activated tooth whitening procedure.
Figure 3:
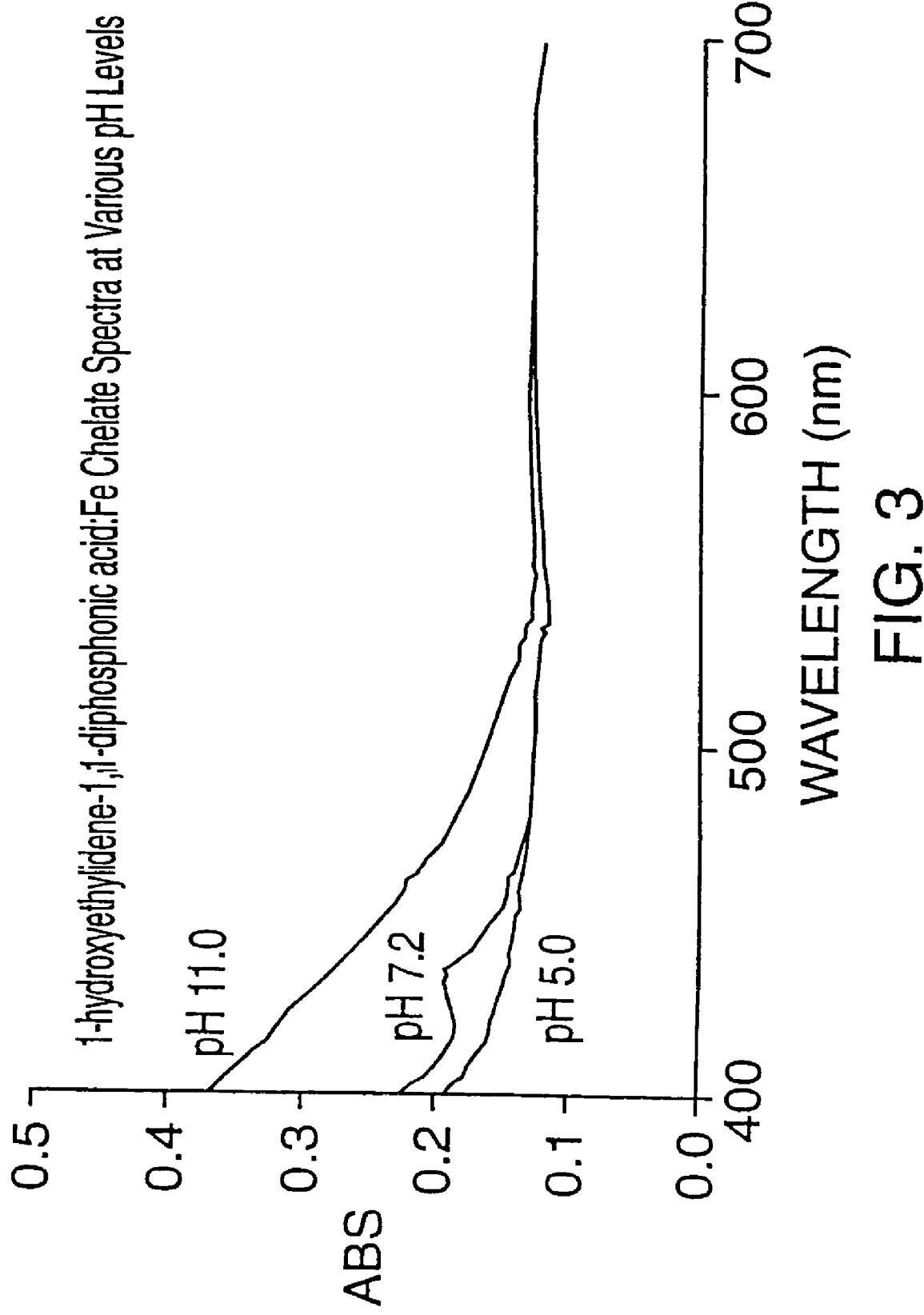
FIG. 3: Graph of Comparative Spectra

Although FIGS. 1 and 2 illustrate embodiments having 3 outputs and 6 outputs, respectively, it is contemplated that the device may have any number of outputs or emitters, from one to a high multiple of outputs, each output consisting of an individual fiber or fiber bundle that ultimately is connected to a light source. The embodiments of a device for the simultaneous and uniform illumination of at least eight central teeth in both the upper and lower arches were described in U.S. application Ser. No. 09/233,793, which is herein incorporated by reference. A preferred embodiment of this device has three linear optical outputs precisely positioned on three front (patient facing) surfaces. A more preferred embodiment of this device has two three bar devices stacked one on the other resulting in six optical outputs on the front patient facing surfaces. Other embodiments of this invention include any number of outputs or emitters, from one to a high multiple of outputs. Each output can comprise an individual fiber or fiber bundle that ultimately is connected to a light source. Embodiments having 3 or 6 outputs are presently preferred for the device because they achieve fairly uniform illumination of the eight or more central teeth without excessive manufacturing problems or costs. More than six outputs, of course are feasible and may in fact be beneficial in terms of uniformity of illumination.

The front surfaces of the device are positioned to give an output configuration such that the combined beams from each optical output converge to illuminate at least the eight central teeth in both the upper and lower arches or the are from the incisors to the first pre-molars in each half arch, a total area of about 10.4 $cm^2$ in the average male. Although depicted in FIG. 1 as linear in form, these outputs may be of any shape, e.g., circular, triangular or linear. Linear forms are preferred. The preferred embodiments have six linear outputs, each output having a length to width ratio of about 16±20%—i.e., ratios of 12.8 to 19.2. In the most preferred embodiment, 80% of the light projected from the outputs onto the 8 upper and lower central teeth is within an area between about 0.9 and about 1.5 inches wide, the approximate distance from the top of the enamel of the top teeth to the bottom of the enamel of the bottom teeth. Each optical output preferably is connected to a distal light source by two glass or plastic fiber optic bundles which originate at the distal light source, enter the device through a socket 20 and terminate at the trifurcated linear output window. Non-uniformity in fiber transmission is generally observed to be minor in the absence of actual breaks in the fibers. Variation in optical output from point to point at the surface of each output or emitter should be no more than about ±10%.

Whether illumination of the stained teeth is performed individually or as a whole, the light emerging from a direct or indirect source may be continuous ("on" the entire procedure), interrupted continuous (primary "on" with short rest interruptions), pulsed ("on" and "off" in a predetermined timed sequence and intensity), or a combination of continuous, interrupted continuous and pulse. In a preferred embodiment from about 10 to about 200 milliWatt/$cm^2$ of light is applied continuously to the front surface of the teeth for a total period of time from about 10 to about 90 minutes. In a more preferred embodiment from about 100 to about 160 milliWatt/$cm^2$ of light is applied continuously or continuously with short interruptions to the front surface of the teeth for a period of time from about 10 minutes to about 30 minutes followed by an interruption or "off" period of about 1 to 10 minutes, with the cycle repeated for a total time of approximately 40-60 minutes. In one envisioned embodiment of the invention a feed-back mechanism based on reflectance would be used to monitor bleaching efficiency and regulate the total amount of actinic radiation applied. In all embodiments of the invention the positioning of the light source affects the energy density applied to the teeth as power density decreases with distance. The preferred placement of the light source will vary depending on the precise nature of the device. For the device described above, the preferred distance for placement of the device is from directly in front of the surface of the teeth up to about 2.0" in front of the surface of the teeth (when measured from the middle of the light source to the central tooth), with a distance of about 1.75" being most preferred.

Figure 5:
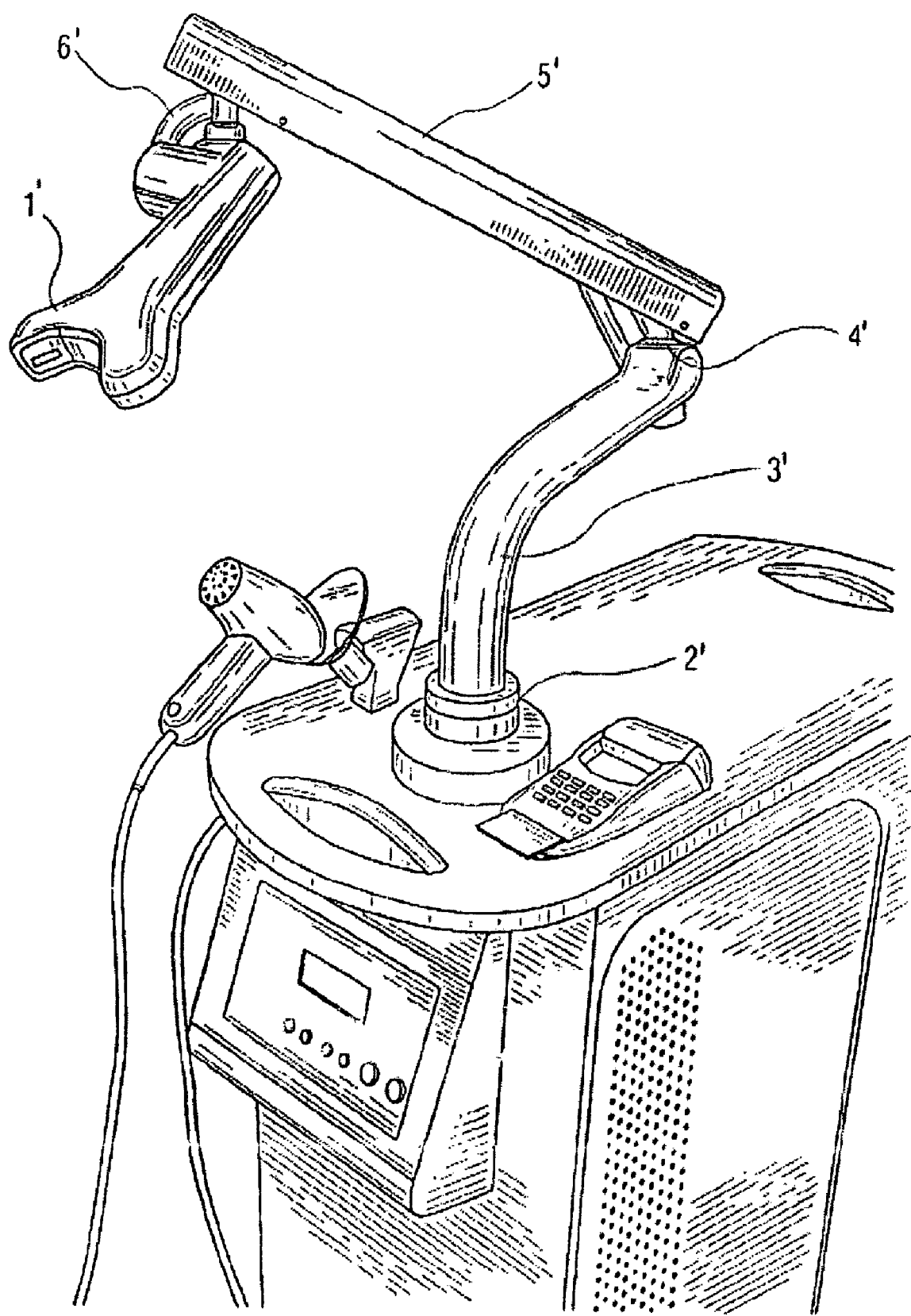
FIG. 5: Shows a portable tooth whitening device

A further development of this device described above is a portable tooth whitening device which is shown in FIG. 5. This portable tooth whitening device comprises one or more lamps capable of treating any number of teeth. In a preferred embodiment, the portable tooth whitening device can simultaneously treat at least 16 teeth at one time. The portable tooth whitening device further comprises a fiber optic delivery system, a flexible articulated arm, and a portable support structure which is on wheels. Preferably the portable tooth whitening device of the invention has a control panel. In a more preferred embodiment the portable tooth whitening device has a key card system for controlling access and usage. Preferably the key card system is the Bull®SafePad® reader with Smart Card®.

Preferably the device of the invention has a curing lamp in a holster. A preferred curing lamp is a Demetron®. Preferred curing lamps emit light in about the blue wavelength region. Preferably the curing light has a light filter to protect the eyes of the operator of the device from errant light from the curing lamp.

A preferred portable support structure has dimensions of about 24"×15", by 31" high and an arm assembly which adds about another 20" in height in the stowed position.

The control panel has an on/off button, a calibration button, and buttons to control the illumination time. The calibration button calibrates the system to insure that the energy setting is correct. Preferably the control panel is at an inclination from the vertical of about 45° so that it can be easily viewed by the operator.

The entire portable tooth whitening device is on wheels and has a flexible arm. It is portable and can be rolled about on the wheels. The arm has glass or plastic fibers, for transmitting light, attached to a structural support. This structural support, as shown in FIG. 5, provides a flexible arm with a wide range of articulation which enables the system to be used in any dental setting and with patients in a wide range of positions. For example, the portable tooth whitening device of the invention can be used in such dental settings as typical dental offices, orthodontic offices, spas in cruise ships, and the like. It can also be moved out of the way for easy storage. The flexibility of the arm allows for the output to be positioned at any angle necessary for whitening the teeth of a patient in either a reclining position or a sitting position, or any angle in between. For example, the head region of the light 1', as shown in FIG. 5, can be in a horizontal position for treating a patient in a sitting position. The head region can be adjusted to an about vertical disposition for treating a patient in a reclining position. The head region can also be adjusted to any other angle between the horizontal and vertical positions. The flexibility of the arm further enables the portable tooth whitening device to be used on either the left or right side of the dental chair.

In a preferred embodiment of the invention, the flexibility of the arm is conferred by the structural arrangement shown in FIG. 5 which has three knuckles with large ranges of motion.

More specifically, knuckle one 2', which is nearest to the table, has an almost 3600 range of motion about an axis vertical or approximately vertical to the table. Knuckle two 4', which is disposed between a first support arm 3' and a second support arm 5' also has an almost 360° range of motion about an axis vertical or approximately vertical to the table. Knuckle two 4' also has a range of motion in the vertical direction of approximately ±45°. Knuckle three 6', which is disposed between the head region 1' and the second support arm 5' also has an approximately 360° range of motion about an axis which is vertical or approximately vertical to the table. Knuckle three 6' also has a vertical range of motion of approximately ±90°.

A number of different sources of actinic radiation have been shown to have utility in the practice of the present invention. In general, any light source capable of emitting actinic radiation in the wavelength range necessary to activate either the inventive photosensitizer(s) or otherwise raise the energy state of tooth chromogens, is contemplated to have utility in the practice of this invention. In particular, light sources capable of emitting actinic radiation that is both biologically safe and effective are preferred, especially those sources which emit limited amounts of infrared light (700 nm and above). Infrared light more readily penetrates the tooth structure and may cause an excessive temperature rise in pulpal tissue.

It is preferred that light sources (combined with filters) emitting only those wavelengths necessary for the activation of the inventive photosensitizer and/or the activation of a tooth stain chromophores be used in the process of whitening teeth with the inventive compositions. It is generally accepted that a pulpal temperature rise of more than 5.5° C. for a significant period of time can be irreversibly damaging to the tooth structure.

More specifically, light sources which emit actinic radiation in the wavelength range from about 350 nanometers to about 700 nanometers are especially preferred, in that both the photosensitizers described herein and the tooth chromogen molecules responsible for tooth staining absorb primarily in this region of the spectrum. Light sources which emit actinic radiation in the wavelength ranges from about 400 and about 505 nanometers are most preferred. Output uniformity should be about +/−10% over the area of the beam once transmitted through a glass or plastic fiber to the optical output which may be placed in front of a patient's teeth. Although there are no limitations on the input and length dimensions of such a fiber, one of about 10 millimeters in diameter and 3 meters (about 10 feet) in length is preferred. Again, although there are no limitations on the input and length dimensions of such a fiber, for the portable tooth whitening device it is preferable to use one of about 10 millimeters in diameter and about 6.5 feet in length. Such energy may be provided by a source which generates a continuous electromagnetic spectrum filtered to the preferred wavelengths with a variation of no more than about +/−10%, or by a source which generates an emission line spectrum, or a combination of both. Suitable lamps which emit actinic radiation in the preferred range of wavelengths include linear flash lamps, tungsten halogen, metal halide, Xenon short arc, Mercury short arc, Mercury Xenon short arc, Argon plasma arc, and Argon short arc lamps, diode lasers and light emitting diodes (LEDS), among others. The output of two Mejiro BMH 250 watt metal halide lamps filtered through dichroic filters to between about 400 and 505 nanometers meet these criteria.

Figure 6:
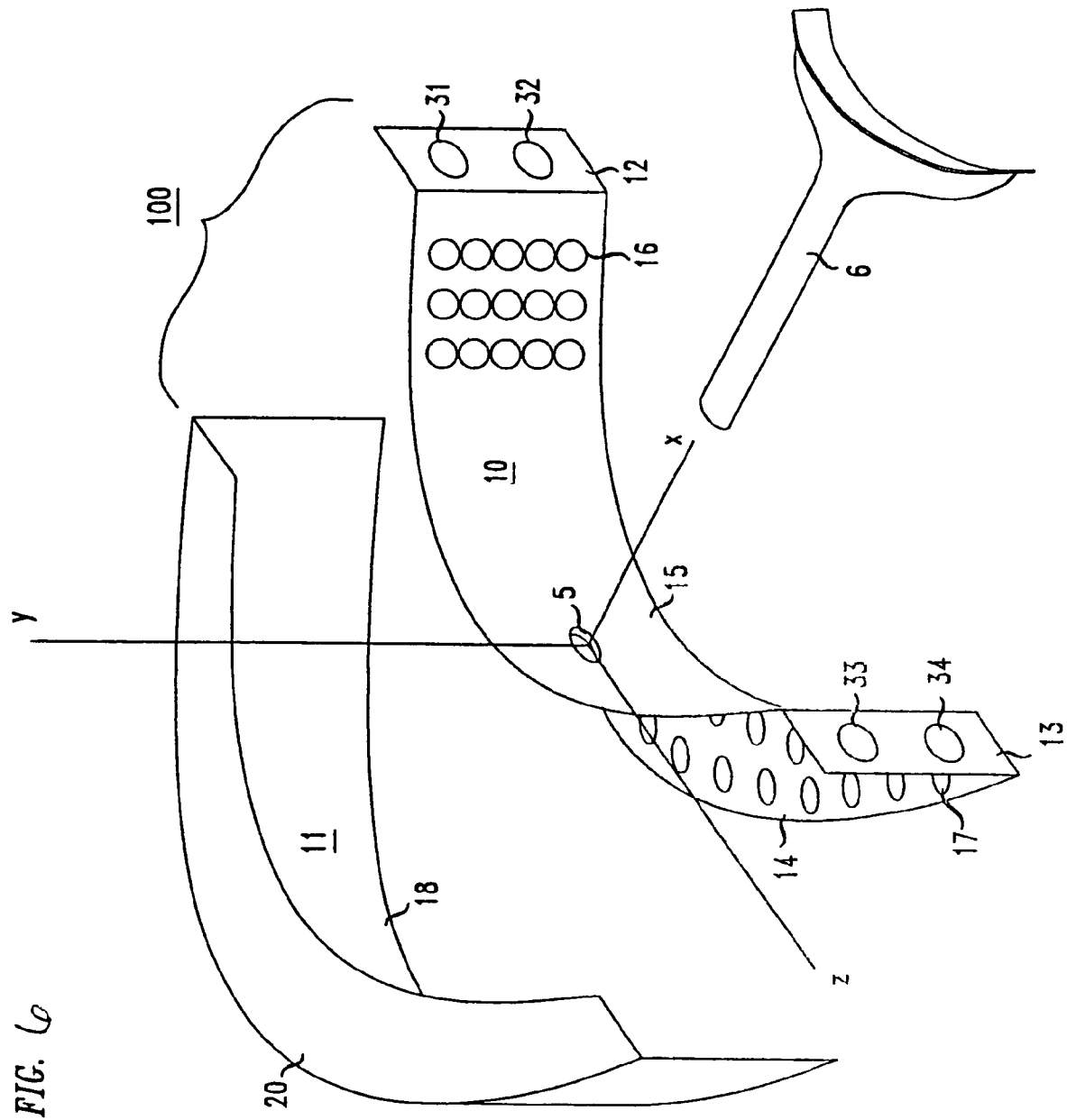
FIG. 6 presents an exploded perspective view of an illustrative embodiment of a tooth whitening assembly in conformance with the principles of this invention.
Figure 7:
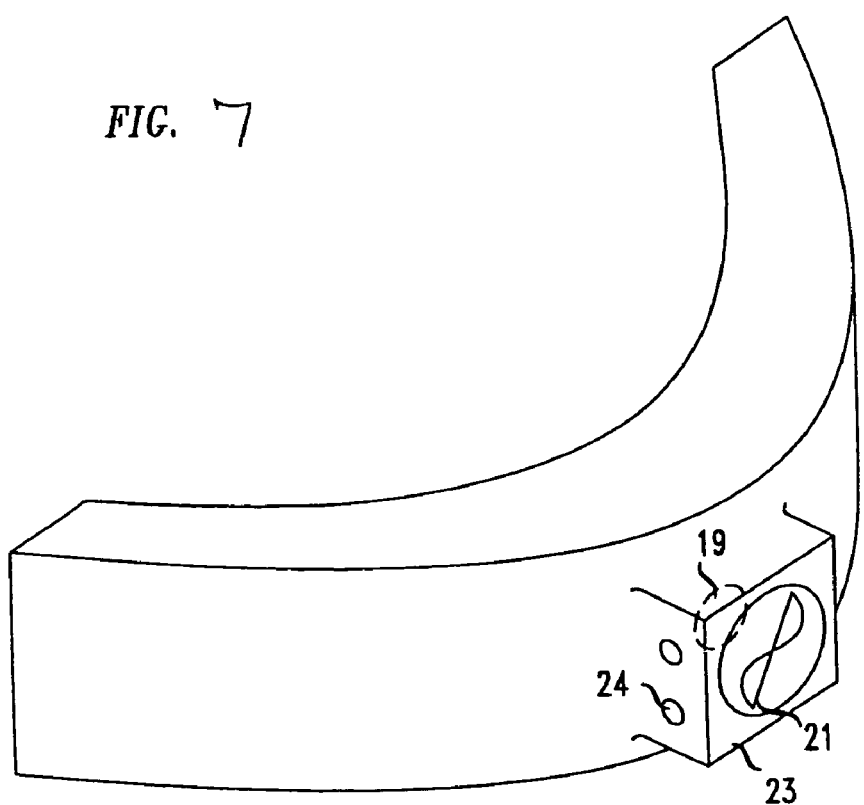
FIG. 7 is a back view of the illustrative embodiment.

Another embodiment of the invention provides a mouthpiece having a plurality of light generating devices (such as fiber optic outputs or LED emitters) that can project a relatively uniform field of light energy onto the labial surfaces of the teeth. The mouthpiece can have a shape substantially like the dental arch. However, mouthpieces of all shapes can be made to project a uniform field of light onto the labial surfaces of the teeth. The term field of light, as used in this specification, means light projected onto a surface. The term uniform field of light, as used in this specification, means that the energy density remains constant over the surface onto which the light is projected. FIG. 6 presents a perspective view of an illustrative mouthpiece 100, comporting with the principles of this invention, with the two main components of this embodiment (elements 10 and 11), being separated for sake of clarity. FIG. 7 shows a perspective back-end view of element 11 of FIG. 6. Mouthpiece 100 is constructed by joining elements 10 and 11, for example, with glue.

Element 10 has a curved member 15 with side walls 12 and 13 at the terminating edges of curved member 15, and a crescent-shaped ledge 14 extending perpendicularly away from the convex surface of member 15. Coordinates x, y, and z are included in FIG. 6 to assist in describing the elements. With reference to these coordinates, the concave surface of member 15 is symmetric about the x axis, perhaps following a parabolic curve that might be defined by the equation $x=a \cdot z^2$ for $|y| \leq y$ and $0 \leq z \leq z$, where a is a positive constant. Member 15 may be said to be concave in the x and z dimensions, and linear in the y dimension. An archway is thus formed by member 15 in the space where $0<x>a \cdot z^2$. The crescent-shaped ledge 14 lies on the x-z plane at y=−y, between the curve $x=a \cdot z^2$ and curve $x=(a+\Delta) \cdot z^2-b$, $\Delta$ and b being positive constants. On the concave surface of member 15 there is a plurality of light-generating devices 16, for example, light emitting diodes (LEDs). In FIG. 6, the LEDs are arranged in an array having columns. Ledge 14 includes an array of holes 17.

Element 11 has a curved member 18 that has a slightly larger curvature than the curvature of member 15 (e.g., following the curve $x=(a+\Delta) \cdot z^2-b$). Aside from being positive, the constants $\Delta$ and b are adjusted so that the vertical edges of curved member 18 mate with the outside edges of walls 12 and 13 when the curved bottom curved edge of member 18 mates with the outside curved edge of ledge 14. Element 11 also has an upper ledge 20 that the same shape as ledge 14.

Thus, when elements 10 and 11 are mated, a hollow space is created within the resulting mouthpiece 100.

Element 11 also has a circular opening 19 (see the perspective back view of element 11 in FIG. 7) roughly at the center of member 18 (shown in FIG. 6), and on the convex side of member 18 there is a housing 23, substantially covering opening 19, within which a fan 21 is installed. The fan is arranged so that when elements 10 and 11 are mated and, as indicated above, a hollow space is created within the mouthpiece, fan 21 causes air to be drawn out of the hollow space of mouthpiece 100, with air being sucked into the hollow space through the array of holes 17. This air draws out the heat that is generated within mouthpiece 100 by virtue of the inherent inefficiencies in converting electrical energy to light (in the light-generating devices).

It should be understood that, with reference to the elements described so far, the most important aspect of mouthpiece 100 is the fact that light-generating devices are situated on the mouthpiece and arranged to face the teeth of a patient. Other relatively important aspects of the elements described so far are the concave, substantially symmetric, surface of mouthpiece 100, and the means for passing air through the mouthpiece.

Figure 8:
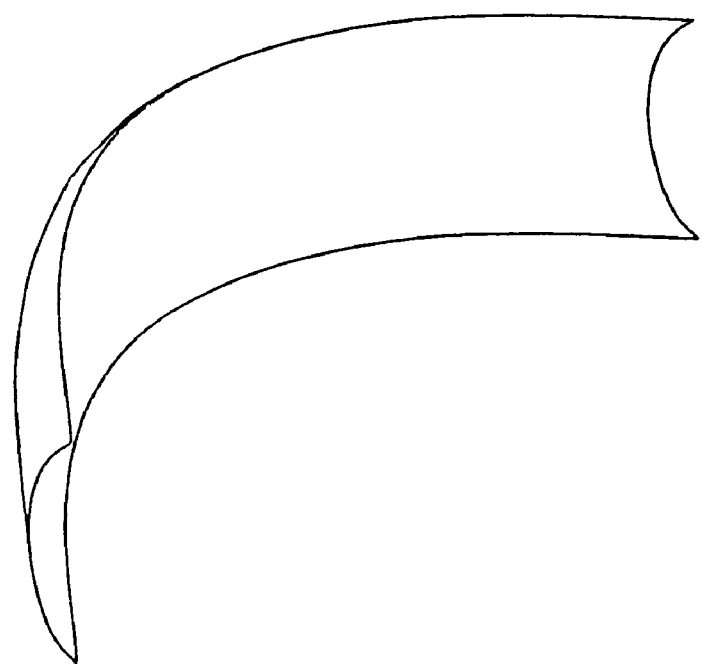
FIG. 8 shows a surface on which light-generating devices are positioned that is curved in three dimensions.

A concave surface on which the light-generating devices are placed is preferable because it more easily allows the creation of a relatively uniform field of light intensity (power per unit area) at a patient's teeth, which are situated within gums that form a generally symmetric and convex surface. Other shapes are possible, of course, with some being less conducive to focusing of light onto a patient's teeth (for example, a flat surface 15), while others being more conducive to focusing of light onto a patient's teeth (for example, a surface that follows the equation $x=a \cdot z^2+b \cdot y^2$, as shown in FIG. 8).

The means for passing air is advantageous because, at least with present day technology, the known light-generating devices that can be placed on surface 15 generate heat as a natural by-product of the inefficiency associated with converting electrical energy to light. One might think of it as "I²R heat." It has been determined that it is best to remove this heat by blowing air through mouthpiece 100, exiting away from the patient's face. Accordingly, the disclosed embodiment includes holes 17 and opening 19 at the back of element 11, housing 23 and fan 21. This, of course, is merely illustrative, and other methods for removing the heat may be employed.

For example, housing 23 can be merely a nipple to which a hose is attached. Fan 19 (or any other device for creating a pressure differential) might be on the remote end of the hose.

Returning to the description of the mouthpiece in FIG. 6 the mouthpiece 100, side walls 12 and 13 include two light emitting diodes each (31, 32, and 33, and 34, respectively) which are useful for guiding the position of mouthpiece 100 in front of the patient's teeth (an example of an index and locator). These diodes may be conventional LEDs that emit light in the visible range (e.g., red) and include focusing lens, designed to create a light beam that points in a preselected direction. Specifically, the light beams that are created by LED 31 and 32 are arranged to meet at a preselected point in space, and that point may be selected to be on the surface of a patient's face when mouthpiece 100 is positioned at its proper place relative to the patient's mouth in order to achieve good teeth bleaching results from the light emitted by the light-generating devices of surface 15. To achieve such beam positioning, the beam created by LED 31 may be tilted toward LED 32, and the beam created by LED 32 may be tilted toward LED 31. Advantageously, the beams are focused to a point at the very spot where the two beams (from LED 31 and 32, respectively) meet, but that is not a requirement. Collimated beams can be used, as well as beams that diverge slightly. The lenses required for creating the beams of LEDs 31 and 32 are perfectly conventional. The pair of LEDs 33 and 34 are arranged in the same way as the pair of LEDs 31 and 32. It should be understood that using a pair of LEDs is merely illustrative. Even one LED may be used, for example, if it is focused to effectively a point at a predetermined distance from surface 15. Certainly, it is also possible to use more than the two pairs of LEDs shown in FIG. 6.

Again, the positioning approach that involves the use of the above-described LED pairs is merely illustrative of an index and locator. It has the advantage of not requiring anything of the patient except sitting still. Another illustrative positioning approach is suggested by dimple 5 (another example of an index) in FIG. 6. This approach, which is quite simple, requires the patient to bite on a positioning device, not unlike bite block 6, depicted in FIG. 6, and requires the positioning of the end of device 6 (an example of a locator) that is distal to the patient in dimple 5 of surface 15.

Figure 9:
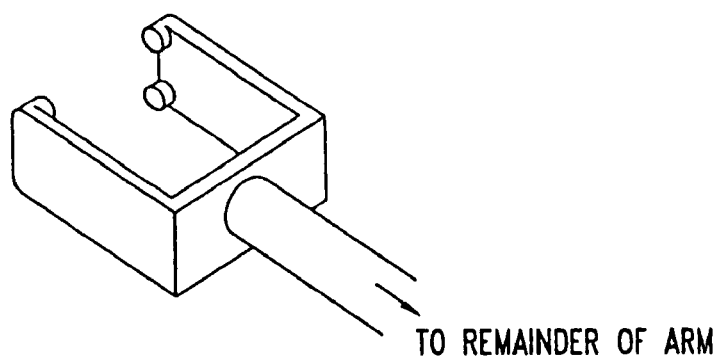
FIG. 9 presents an illustrative end-piece of an arm arrangement to which the FIG. 6 assembly may attach.

Directing attention to FIG. 7, housing 23 includes circular indentations 24, which form the means for connecting mouthpiece 100 to an arm arrangement that is not unlike the conventional arm arrangement to which a dentist's light is attached. Such an arrangement includes an end piece for coupling housing 23, for example, as illustrated in FIG. 9.

Ideally, in providing a catalytic light to the surface of a patient's teeth, each portion of each tooth would get "just the right amount of light." However, the situation presents many variables that are difficult to control or ascertain (e.g. shape of teeth, size of teeth, distance of teeth from the points of focus on the patient's face, etc.) and, therefore, one has to deal with "roughly the right amount of light." It has been found that a reasonable goal in connection with the user of this invention to provide a substantially uniform light intensity to all of the teeth, and to direct as much of the available light to the teeth.

Figure 10:
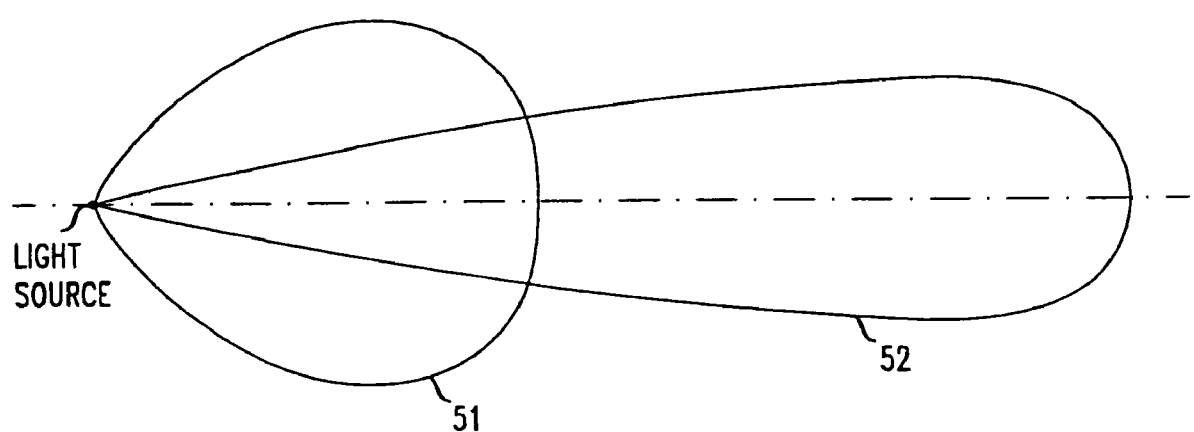
FIG. 10 illustrates the light profile of a light-generating device, as well as the profile that may result from focusing of the light.

Most devices that generate light do not generate collimated light but, rather, create a light beam that expands with distance from the light source. Ideal point sources generate light that is uniform (in intensity) in all directions. That is, at any point in space, the light intensity corresponds strictly to the distance of the point from the point source. Stated differently, all points on a hemisphere centered about the point source receive the same light intensity. In two dimensions, this can be represented by a semicircle centered on the point source, because the distance from the center to any point on the semicircle (corresponding to the magnitude of the intensity vector) is a constant. Non-ideal light sources do not produce the same light intensity in all directions and, typically, the highest intensity is some direction that is related to the structure of the light-generating device. LEDs, for example, typically produce the highest light intensity at a direction that is perpendicular to the surface of the LED's semiconductor substrate. In two dimensions, the light intensity profile of a non-ideal light-generating device might be something not unlike curve 51 of FIG. 10. At angles close to the aforementioned perpendicular, the light intensity—represented by the length of the vector from the origin to curve 51 is high. At angles significantly away from the perpendicular, the light intensity is lower; and at angles that are close to 90° from the perpendicular, the light intensity is practically zero. The light emanating from ideal, as well as non-ideal, light sources can be focused with a lens, for example, to generate a light intensity profile curve more like curve 52. It should be remembered, by the way, that curves 51 and 52 are a light intensity profile curves when viewed in two dimensions. They represent three-dimensional surfaces (akin in shape to hot air balloons) that are often referred to as "lobes."

Figure 11:
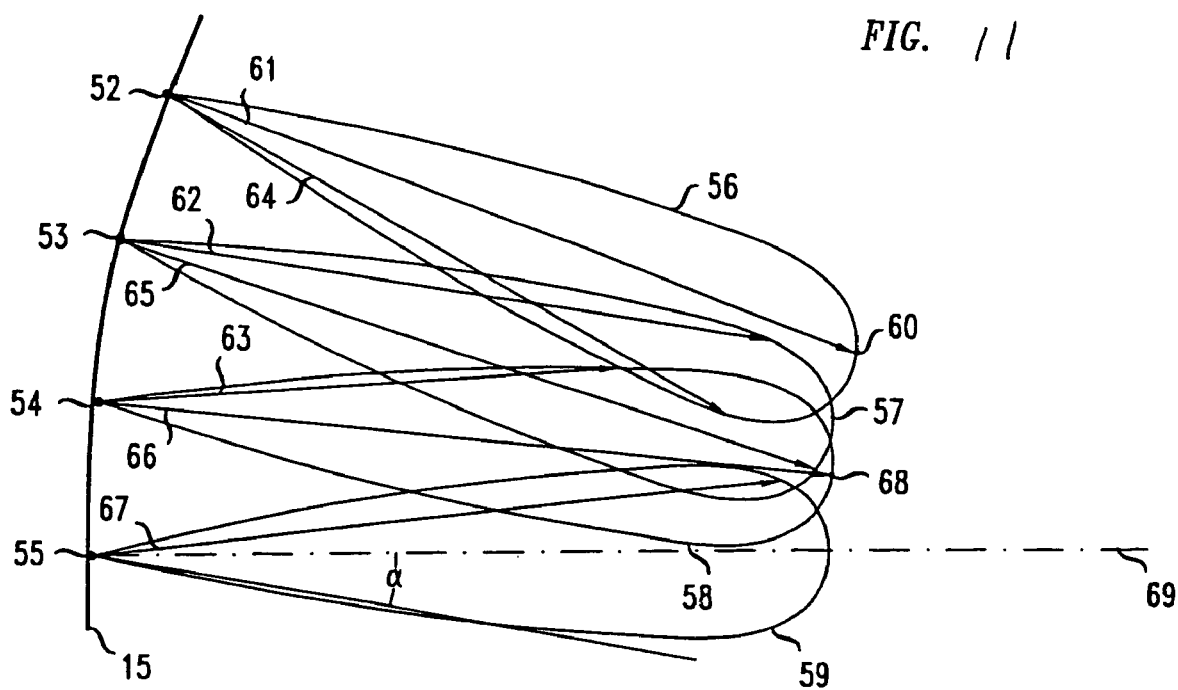
FIG. 11 shows surface 15, a plurality of light profile lobes that emanate from light sources at surface 15, where the lobes are directed to overlap and where, consequently, the beams add on a power basis to form a combined field of light.

Given a light intensity profile curve, and given that the light-generating devices 16 in a row on surface 15 (i.e., on an x-z surface) are spatially separated from each other, if the light-generating devices 16 are non-coherent, the light intensity profile that results from a plurality of lights along a row on surface 15 corresponds to the power addition of the individual light intensity profile curves. To illustrate, FIG. 11 shows light-generating devices 52, 53, 54 and 55 (with appropriate lenses) within a row on surface 15 that generate light beams with light intensity profile curves 56, 57, 58 and 59, respectively. Those light beams add (power addition) so that at point 60, for example, the light intensity corresponds to a sum of three factors: one related to the length of vector 61, one related to the length of vector 62, and one related to the length of vector 63. Note that beam 59 contributes no light at point 60. At point 68, for example, the light intensity corresponds to a sum of four factors: one related to the length of vector 64, one related to the length of vector 65, one related to the length of vector 66, and one related to the length of vector 67.

It is noted that FIG. 11 shows all of the light-generating devices producing identical light intensity curves that are symmetric about an axis of symmetry (e.g. axis 69 of curve 59). Moreover, the axes of symmetry are perpendicular to the tangent of curve 15 at the situs of the light sources (e.g., source 55). Given that a generally uniform light intensity is desired at a surface of the patient's teeth, a designer of mouthpiece 100 has numerous parameters under his or her control that allow the designer to achieve this goal. That includes:

the curvature of surface 15;
the spacings between the light-generating devices along a row of surface 15 (which do not have to be uniform);
the overall light intensity emitted by the individual light-generating devices (both, buying light-generating devices that produce different amounts of light for a given amount of driving current, and driving the light-generating devices with different amounts of driving current);
the shapes of the light intensity profile curves (controlled by the lens of the light-generating devices); and
the directions of the axes of symmetry of the individual light-generating devices.

It should be also remembered that the light produced by the light-generating devices serves as a catalyst that speeds up the bleaching process in teeth whitening, and that time of exposure is also a variable that can be employed. That is, it bears remembering that it is not just light intensity per se that is important, but the integral of the light intensity over time that is important.

Figure 12:
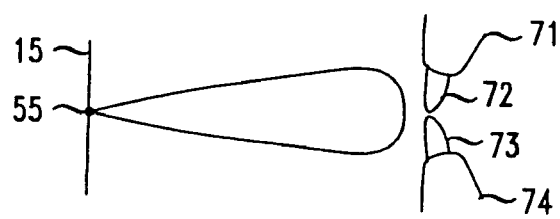
FIG. 12 depicts an arrangement with a single row of light-generating devices.

The discussion above basically addresses the two dimensions represented by the x and z axes of FIG. 6. Of course, mouthpiece 100 is a three-dimensional object with light-generating devices both in rows along the curvature of surface 15, and in columns that are perpendicular to the rows. Further, the generally uniform light intensity that is desired is over a surface in which the patient's teeth are found; which is a surface that is roughly convex in the x-z axes, and roughly independent of position along the y axis, within a certain distance from the origin. In other words, it is a surface that roughly mates with surface 15. If the light-generating devices are capable, in aggregate, of generating a sufficiently intense light, in the range of 10 to 300 mw/cm$^2$ at the surface of the teeth, and if the lens that are integral with the light-generating devices are designed to provide—when aggregated over the row of light-generating devices—a substantially uniform light on the upper and lower teeth of a person, as shown in FIG. 12, then a single row of light-generating devices in mouthpiece 100 would suffice.

The above-mentioned range of light intensities is fairly broad, but that is because the duration of time that light needs to be applied to a patient's teeth or order to get a specific beneficial results is inversely proportional to the intensity of light applied to a patient's teeth. Hence, with a low intensity of light the procedure takes a long time, and with a high intensity of light the procedure takes a short time. While a simple tradeoff of time for intensity is technically acceptable, it has been concluded that the above-mentioned range comes close to the commercially acceptable procedure-time limits. We find that an intensity that is nominally set at 130 mw/cm$^2$ (i.e., 130±10 mw/cm$^2$) works well to get a beneficial result in one hour. Higher intensities are, of course, permitted to be used, and we believe that a light intensity of as much as 200 mw/cm$^2$ is still safe.

Aside from the commercial notion that one might not wish to have a procedure that takes hardly any time, because it is difficult to charge a reasonable fee therefor, in today's technology there is an additional reason to be concerned with very high intensities, and that is heat. That is, although the physiological effects of heat are most pronounced for radiation in the infrared (IR) wavelengths of light (750 nm to 2,500 nm), there is some perception of heat at somewhat shorter wavelength as well. The light wavelengths at which the light-sensitive bleaching gels used in today's practice benefit from the application of light are in the 300 to 900 nm range. Clearly, there is an overlap between wavelengths at which the bleaching gels are effective, and wavelengths that produce heat. Compounds can be selected that are most strongly activated with light that is closer to the blue/violet side of visible light, and heat from sources that produce such a light does not present a problem. However, even light sources that produce a preponderance of light intensity in the blue/violet range nevertheless produce some light in the IR range and, moreover, produce a fair amount of heat from the inefficiencies in the conversion of electrical energy into light. Further some devices (such as LEDs) are current devices that are typically controlled with a voltage and a series resistor, and such resistors produce heat. That heat is extracted from mouthpiece 100, as described above, with fan 21.

We have discovered that the objects of this invention can be satisfied with LEDs that produce light having a bulk of their energy in the range of 475±40 nm. Such LEDs can be obtained, for example, from the US distributor of Nichia (a Japanese LED manufacturer). It is noted that the Nichia LEDs can be obtained with two types of integral lenses. One that produces a cone of 15°, and one that produces a cone of 30°. A cone of 15° means that the angle α (see FIG. 11) between the center of symmetry and the point along the light intensity profile curve where the intensity is one half the peak intensity is 7.5°.

Figure 13:
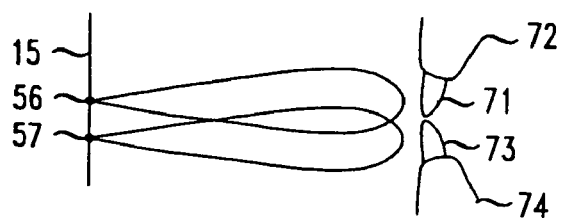
FIG. 13 depicts an arrangement that employs only two rows of light-generating devices in the FIG. 6 assembly.

Returning to the question of the necessary number rows of light-generating devices on surface 15, with today's technology it is unlikely that a single row of devices would suffice (from the standpoint of the light intensity that can be generated from an LED) and, because of that, the FIG. 6 mouthpiece is shown with a plurality of light-generating devices arranged in columns. FIG. 13 shows an arrangement where a column of light-generating devices has only two devices: 56 and 57. With a reasonably simple lens design the row of light-generating devices that contains device 56 can handle the upper teeth of a patient (e.g., tooth 71 attached to upper gum 72), and the row of light-generating devices that contains device 57 can handle the lower teeth of a patient (e.g., tooth 73 attached to lower gum 74). If one row of devices (per tooth) is not sufficient because of light power output limitations of the devices used, or because a single device cannot provide the desired uniformity of light intensity on the teeth, a plurality of light-generating devices that is greater than two devices per column might be used, and appropriately focused. One might note that the light profile of the light-generating devices of FIG. 12 is broader and more flattened (i.e., more equal intensity) in the neighborhood of an axis that is perpendicular to surface 15 than the light profile of the light-generating devices of FIG. 13. This intends to demonstrate the flexibility that a design of the lenses that are placed in front of the light source (whether integral to the light-generating device, and/ or positioned in front of the light-generating devices) can impart.

Figure 14:
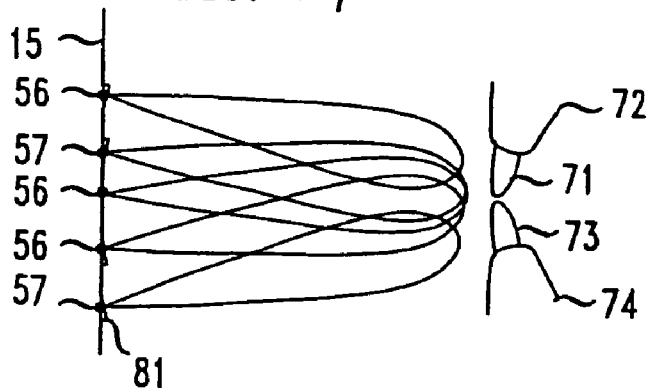
FIG. 14 depicts an arrangement that employs angling pedestal upon which the light-generating devices are placed, thus causing the light lobes from the different devices to be angled toward each other and to thereby to overlap.
Figure 15:
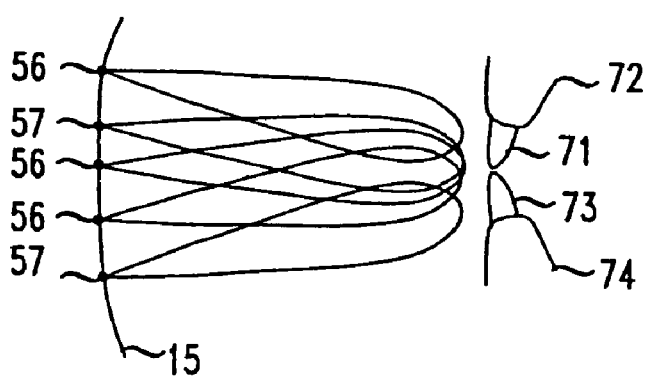
FIG. 15 depicts an arrangement that employs the curvature of surface 15 to cause light lobes to overlap.

FIG. 14 shows an arrangement where 5 LEDs in a column are focused with appropriate lens incorporated in the individual LEDs. When the LED's that can be obtained have built-in lens that output a light beam whose axis of symmetry is perpendicular to the substrate of the LED, then the lobe of the LEDs need to be angled by some other means. One embodiment positions additional lens in front of the LEDs so as to tilt the generated beam in the desired direction. Another embodiment angles the LEDs, as shown in FIG. 14, by means of angling, triangular shaped, pedestals 81 that produce the appropriate tilting. Incorporating the proper angling within the curved surface of member 15 may attain the same results. That is, there is no requirement that the surface of member 15 needs to be a simple, smooth, mathematical curve. Yet another embodiment, which angles the LEDs employs a curved surface like the one depicted in FIG. 8, is shown in FIG. 15. We found that largest angle that is useful to direct a lobe away from the perpendicular is about 15°.

Figure 16:
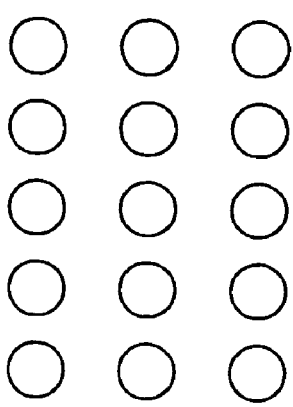
FIG. 16 shows a linear array of LEDs used in the FIG. 1 assembly.
Figure 17:
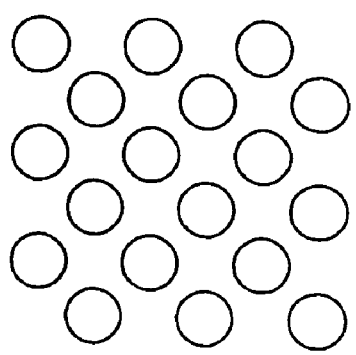
FIG. 17 shown a staggered array of LEDs that may be used in the FIG. 1 assembly.

The FIG. 6 arrangement of the light-generating devices creates a two dimensional array of devices (if surface 15 is "flattened out"). This arrangement, which is also shown in FIG. 16 is not a requirement. The lights can form any desired pattern and, for example, a uniform light intensity pattern may be more easily achieved with a staggered pattern like the one shown in FIG. 17, or even a "honeycomb" pattern.

Regardless of the pattern that is employed, and whether surface 15 is straight, like illustrated in FIG. 13; with angling pedestals like illustrated in FIG. 14, curved like illustrated in FIG. 15, or has a complex shape where different points on the surface have specified normals that are dictated by the directions in which the light lobes need to be pointed to in order to get a uniform light intensity field, the LEDs, can be easily placed on surface 15. That is, the LEDs can be purchased separately (each of which has two electrical leads), surface 15 can be manufactured with a pair of feed-through holes for each LED, and the LEDs are installed by feeding the leads of the LEDs through the feed-through holes.

Figure 18:
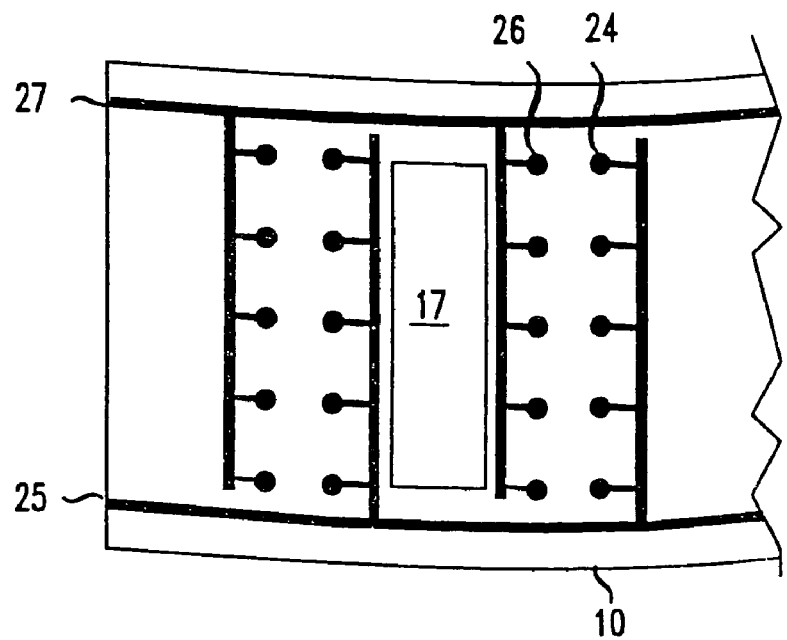
FIG. 18 illustrates an electrical connection of the LEDs on the back (convex) surface of member 10.

FIG. 18 shows a portion of the back view of element 10, with a column of printed-circuit type feed-through holes 24 for the anodes of the LEDs in a column, and an adjacent column of printed-circuit type feed-through holes 25 for the cathode of the LEDs in a column. Holes 24 are connected to bus 26, and holes 25 are connected to bus 27. Buses 26 and 27 are connected to electrical terminals (not shown) through which power is supplied to buses 26 and 27. When the LEDs are inserted into holes 24 and 25 and soldered to the feed-through holes, the construction is complete. It may be noted that LEDs are current devices, in the sense that the light output is a function of the LED current. To impart accurate control over the currents of the individual LEDs, a series current circuit (as simple as a resistor) is advantageously included with each LED, allowing the energy applied to buses 26 and 27 to be a controlled voltage. The current circuit, which is a well-known electrical element is not shown in FIG. 18 for sake of simplicity.

The drawing depicted in FIG. 18 employs a common electrical control of the LEDs inserted into surface 15. A control that is different for each different row, or for each different column of the LEDs is easily implemented with a different wired arrangement on the back end of element 10, including electronic circuits that are placed within the hollow space of mouthpiece 100 to provide individual power control of the LEDs. The electronic circuits can be analog, providing a light intensity control via the magnitude of the voltage applied to the LEDs, or can be digital, providing a light intensity control via duration control of the voltage of the LEDs.

Figure 19:
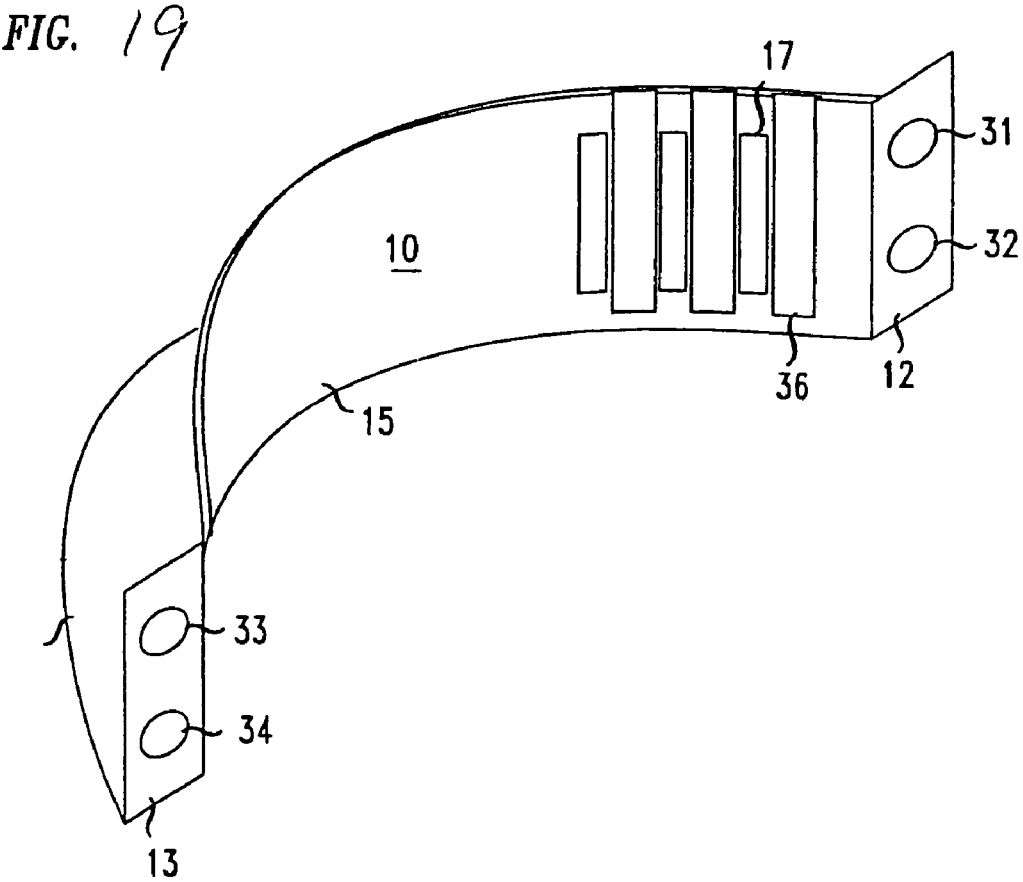
FIG. 19 shows an arrangement for sliding strips that contain LEDs into member 10 of the FIG. 1 assembly.

LED's are generally considered to be very reliable, at least with respect to whether they generate light or not. It is expected that they will not be as reliable with respect to the intensity of the light output. While mouthpiece 100 is fairly inexpensive, in and of itself, there may be arrangements where it would be disadvantageous to replace the entire mouthpiece when one, or a few LEDs start to generate light at below some expected intensity. This is true, for example, when mouthpiece 100 is an integral part of an entire arm assembly. FIG. 19 presents an arrangement where the columns of LEDs are slideably coupled to mouthpiece 100. That is, a plurality of LEDs are manufactured on circuit board strips that are somewhat flexible, as depicted in FIG. 19, with printed circuit board leads on the back, in a manner not unlike the one shown in FIG. 18. Those strips are slid into troughs 36 in surface 15 of element 10 to form mouthpiece 100, and when the strips are properly positioned in troughs 36, the anode and cathode leads of the strip make contact with corresponding contacts on the back of surface 15 to provide the electrical power. Element 10 in the FIG. 19 embodiment needs to be somewhat thicker than element 10 in the FIG. 6 embodiment (when troughs are used), but the difference is not significant.

Figure 20:
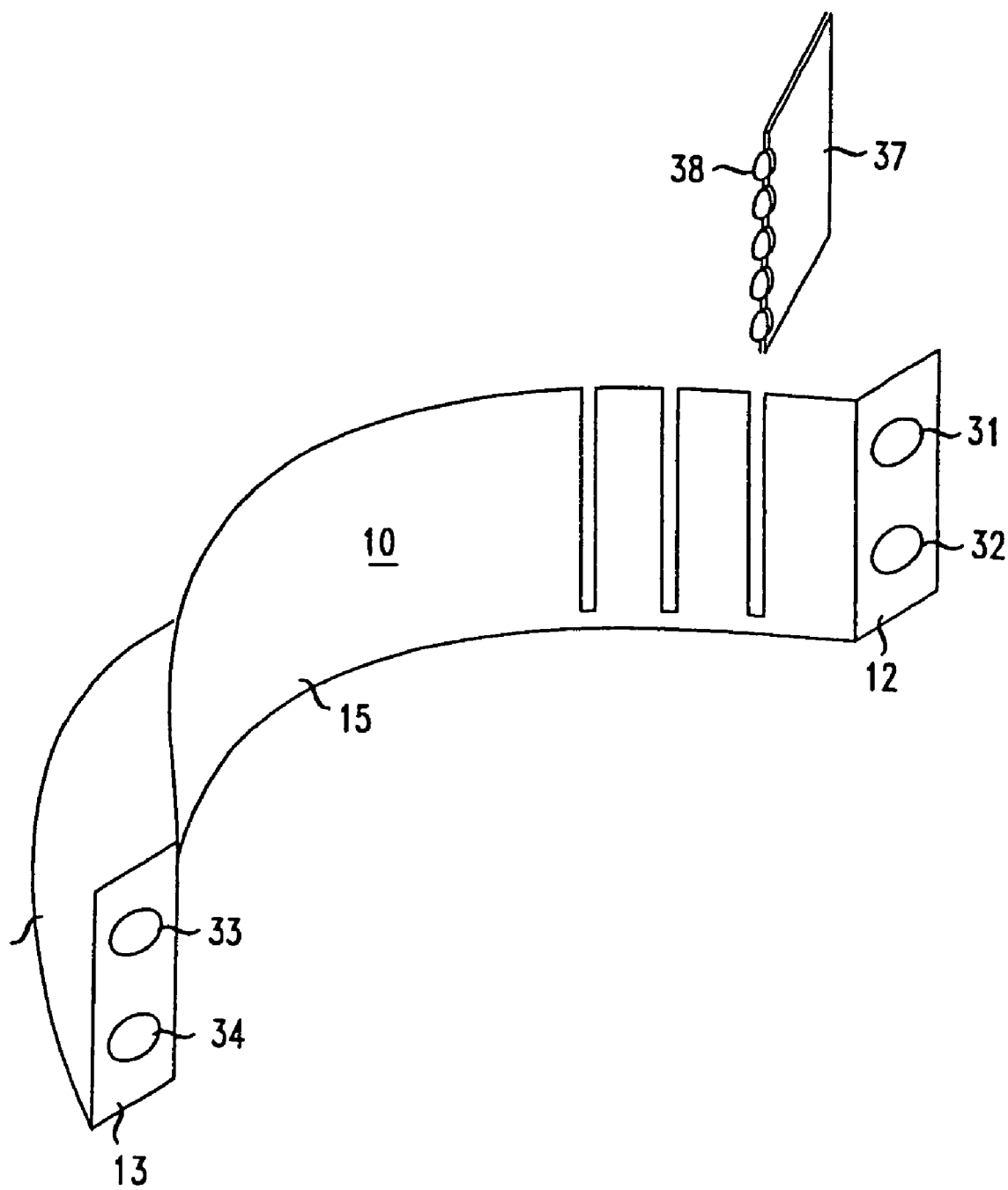
FIG. 20 shows a different arrangement for sliding mini-circuit boards with edge-mounted LEDs into member 10 of the FIG. 6 mouthpiece.

FIG. 20 shows a slightly different embodiment. Instead of sliding in LED-laden strips effectively within surface 15 of element 10, small circuit boards 37 that have edge-mounted LEDs are inserted into element 10 effectively perpendicularly to surface 15 of element 10.

FIG. 6 aims to cover all of the patient's teeth at once. While that is a salutary goal, there are times when only one, or a few, of a patient's teeth need to be whitened. A modified version of the FIG. 6 assembly can be created using the principles disclosed herein, basically employing an assembly with light-generating devices on the assembly, and the light-generating devices—such as LEDs—being selected to produce light in the spectral range disclosed above, focused, and directed so that the lobes of light generated by the LEDs overlap at a preselected distance form the assembly. A health-care professional can then apply the assembly at this preselected distance from the tooth, or teeth of the patient. When it is desired to use such an assembly to whiten the entire set of a patient's teeth, the health-care professional can scan the device over the teeth.

The inventive apparatus, when constructed with multiple LED's arranged in a manner to focus light on the surface of the teeth, demonstrates a surprising phenomenon. A focused LED array, having many relatively low power density point sources of light, creates a "sweet spot" region of higher power density in the vicinity of the focal plane (in the case of an arcuate LED array apparatus for doing tooth whitening, the focal plane has a curvature which runs more or less parallel to the surface of the patient's teeth). A focused LED array can be designed to provide the highest power density within the sweet spot; a patient is then positioned so that her teeth fall within this area to obtain the best effects from the light energy. Not only does the light energy decrease as the patient's teeth are moved further from the focused LED array, but light energy also decreases when the patient's teeth are moved closer to the LED array. This phenomenon provides a high margin of safety for the patient; if the patient accidentally comes too close to the LED array, the power density would be less than that in the sweet spot.

The above discloses the principles of this invention by way of illustrative embodiments. It should be understood that various modifications and additions might be introduced by persons skilled in the art without departing from the spirit and scope of this invention, which is delineated by the appended claims. For example, an additional control variable over the light-generating devices is the size of the devices used (e.g., LEDs with larger, or smaller, active areas). Also, different LEDs in the assembly can be selected to have different spectral ranges.

Further, the positioning of the light-generating devices on the curved surface is shown to be with feed-through holes and with slideable strips. Clip-on strips can also be used. More interestingly, surface 15 can include means to attach a flexible membrane on which the entire plurality of LEDs can be manufactured, for example through a semiconductor growth process. Still further, while the above discusses creating a field of uniform intensity, embodiments may be created to provide whatever light intensity profile may be desired. Yet further, the entire assembly of elements 10 and 11 can be manufactures to allow some flexibility in the shape of curved surface 15. This allows for tailoring of the FIG. 6 device to the shape of the mouth of different patients.

Further, in embodiments where lenses that are not integral to the light-generating means are employed, the lenses can be created as a group, within a clear membrane that is positioned in front of member 15.

The following examples set forth preferred embodiments of the invention. These embodiments are merely illustrative and are not intended to, and should not be construed to, limit the claimed invention in any way.

EXAMPLE I

In order to determine the ability of the inventive compositions to eliminate tooth stain, a preliminary in vitro study on stained bovine enamel was performed. Squares of dental enamel 4 mm on a side were cut, using a diamond-cutting disk, from bovine permanent incisors. Using a mold, the enamel squares were embedded in clear polyester casting resin (NATCOL Crafts Inc., Redlands, Calif.) to provide 1.5 cm square blocks with the labial surface exposed. The top surface of the polyester blocks was ground flush with the leveled labial surface of the enamel squares by means of a dental model trimmer. The surface was then smoothed by hand sanding on 400-grit emery paper using water as the lubricant until all grinding marks were removed. Finally, the top surface of the blocks was hand polished to a mirror finish using a water slurry of GK1072 calcined kaolin (median particle size=1.2 microns) on a cotton cloth. The finished specimens were examined under a dissecting microscope and were discarded if they had surface imperfections.

In preparation for the formation of artificial stained pellicle on the enamel, the specimens were etched for 60 seconds in 0.2M HCl followed by a 30-second immersion in a saturated solution of sodium carbonate. A final etch was performed with 1% phytic acid for 60 seconds, then the specimens were rinsed with deionized water and attached to the staining apparatus.

The pellicle staining apparatus was constructed to provide alternate immersion into the staining broth and air-drying of the specimens. The apparatus consisted of an aluminum platform base which supported a Teflon rod (¾ inch in diameter) connected to an electric motor, which by means of a speed reduction box, rotated the rod at a constant rate of 1.5 rpm. Threaded screw holes were spaced at regular intervals along the length of the rod. The tooth specimens were attached to the rod by first gluing the head of a plastic screw to the back of a specimen. The screw is then tightened within a screw hole in the rod. Beneath the rod was a removable, 300-ml capacity trough, which held the pellicle, staining broth.

The pellicle staining broth was prepared by adding 1.02 grams of instant coffee, 1.02 grams of instant tea, and 0.75 grams of gastric mucin (Nutritional Biochemicals Corp., Cleveland Ohio 44128) to 250 ml of sterilized trypticase soy broth. Approximately 50 ml of a 24-hour *Micrococcus luteus* culture was also added to the stain broth. The apparatus, with the enamel specimens attached and the staining broth in the trough was then placed in an incubator at 37° C. with the specimens rotating continuously through the staining broth and air. The staining broth was replaced once every 24 hours for ten consecutive days. With each broth change the trough and specimens were rinsed and brushed with deionized water to remove any loose deposits. On the eleventh day the staining broth was modified by the addition of 0.03 grams of $FeCl_3.6H_2O$, and this was continued with daily broth changes until the stained pellicle film on the specimens was sufficiently dark. Then the specimens were removed from the staining broth, brushed thoroughly with deionized water, and refrigerated in a humidor until used.

Absorbance measurements over the entire visible spectrum were obtained using the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978). The CIELAB color scale evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

The stained enamel specimens were allowed to air-dry at room temperature for at least one hour before absorbance measurements were made. Measurements were conducted by aligning the center of a 4-mm square segment of stained enamel directly over the 3-mm aperture of the Minolta spectrophotometer. An average of 3 absorbance readings using the L*a*b* factors were taken for each specimen.

The difference between the pre-treatment (baseline) and post-treatment readings for each color factor (L*, a*, and b*) represented the ability of a test solution to eliminate chromogens from the stained teeth.

The overall change in color of stained pellicle was calculated using the CIELAB equation $\Delta E = [(\Delta L^*)^2 + (\Delta a^*)^2 + (\Delta b^*)^2]^{1/2}$ A "Corrected $\Delta E$" value was calculated by eliminating from the above formulation the contribution of any positive $\Delta a$ or $\Delta b$ values (positive $\Delta a$ and $\Delta b$ values are changes in tooth color in the opposite direction from zero, and hence construed to add color, rather than remove it).

The following oxidizing composition was prepared, which contained approximately 15% by weight hydrogen peroxide and 1 percent by weight of the photosensitizer precursor 1-hydroxyethylidene-1,1-diphosphonic acid (Dequest 2010, Monsanto Corp., St. Louis, Mo.). Highly purified water (18.2 megaohm, filtered through a 0.2 micron filter) was utilized in order to maintain good stability of the composition during storage. The composition was thickened with a carboxypolymethylene polymer (Carbopol 974P, B.F. Goodrich Co., Cleveland, Ohio) to the consistency of a light, non-runny gel. Glycerin was added in a small percentage as a humectant and stabilizer (as a free radical scavenger), and the Carbopol 974P was neutralized to a pH of 5.00 with ammonium hydroxide, resulting in the formation of a transparent and thixotropic gel.

| Ingredient | Percentage |
| --- | --- |
| Distilled water | 49.400 |
| 1-hydroxyethylidene-1,1-diphosphonic acid | 1.000 |
| Glycerin 99.7% | 5.000 |
| Hydrogen peroxide 35% | 42.900 |
| Carbopol 974P | 1.700 |
| Ammonium hydroxide 29% | to pH 5.5 |
| TOTAL | 100.000 |

The above composition was prepared in a plastic mixing chamber by combining, under agitation with a Teflon-coated mixing paddle until a clear solution was obtained, the distilled water, the 1-hydroxyethylidene-1,1-diphosphonic acid, and the glycerin. The Carbopol 974P was then sifted slowly into the vortex created by the mixing paddle and allowed to mix until a homogeneous slurry of the polymer was obtained. Finally, the ammonium hydroxide was added in a constant, dropwise fashion over a period of about 5 minutes until thickening and clarification of the slurry occurred. A pH probe was inserted periodically and the ammonium hydroxide addition proceeded until a pH of exactly 5.00 was obtained. The resulting gel contained 15% by weight hydrogen peroxide, and was highly transparent and thixotropic (non-slumping) in character.

Each stained bovine enamel slab was coated with a 1-2 mm film of the composition in Example I above for a specified period of time and exposed to actinic radiation from one of several light sources. Table 1 below shows some comparative results obtained by exposing gel-treated enamel slabs to either Argon plasma arc (AR) or tungsten halogen (TH) light sources. This particular protocol called for the fiber optic light guide to be placed 5 mm from the surface of the enamel during light exposures. The energy of each pulse was adjusted with a power density meter prior to each exposure regimen and measured again after each regimen to verify consistent output of the light source over the duration of the test. The results are listed in Table 1 below:

TABLE 1

| Bovine Tooth # | Light Source | Total Gel Contact Time | Number of Pulses | Energy/Pulse (Joules) | Corrected Delta E* |
| --- | --- | --- | --- | --- | --- |
| B311 | None | 30 min | 0 | 0.00 | 12.76 |
| B388 | AR | None | 30 | 1.66 | 1.41 |
| B277 | AR | 30 min | 30 | 1.66 | 29.28 |
| B214 | AR | 30 min | 30 | 3.35 | 29.75 |
| B283 | AR | 10 min | 10 | 3.29 | 18.62 |
| B147 | AR | 10 min | 10 | 4.90 | 25.98 |
| B401 | AR | 10 min | 30 | 4.97 | 32.18 |
| B211 | AR | 5 min | 15 | 4.84 | 20.05 |
| B213 | AR | 5 min | 30 | 4.93 | 31.02 |
| B35 | TH | 5 min | 15 | 1.29 | 12.88 |
| B35 | TH | 5 min | 15 | 1.29 | 19.39 |
| B35 | TH | 5 min | 15 | 1.29 | 20.01 |
| B35 | TH | 5 min | 15 | 1.29 | 23.61 |
| B35 | TH | 5 min | 15 | 1.29 | 25.35 |
| B35 | TH | 5 min | 15 | 1.29 | 26.41 |

*Elimination of positive $\Delta a$ and $\Delta b$ values from calculation

The data in Table 1 demonstrates that:

(1) In the in vitro model described, exposure of bovine enamel slabs, contacted with the inventive gel composition above, to pulsed actinic radiation from a Argon plasma arc light source resulted in significantly reduced tooth stain as compared to slabs treated either with just gel alone (and not exposed to the light source) or light source exposure only (no gel).

(2) Six sequential treatments (over 30 minutes) of a single stained bovine enamel slab (B35) with gel and concurrent exposure of said slab to pulsed actinic radiation from a tungsten halogen light source (5 minute exposure periods) resulted in an increasing level of tooth stain removal over the period of the test. The result was significantly lighter in color than that achieved in tooth number B311, which was also in contact with the inventive gel composition, but did not get exposed to a light source.

EXAMPLE II

Figure 4A:
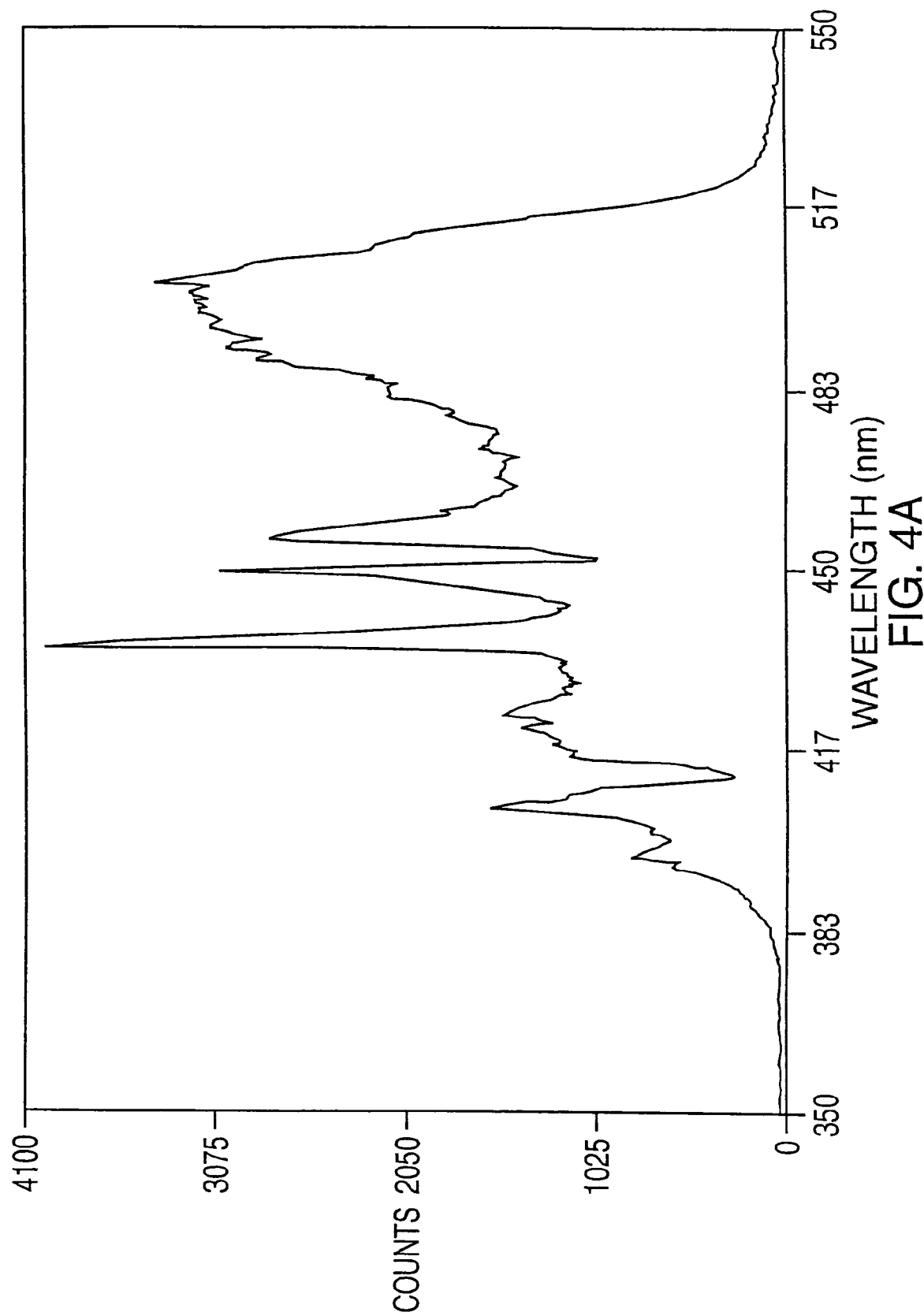
FIG. 4: Spectral Curves of Light Attenuation
Figure 4B:
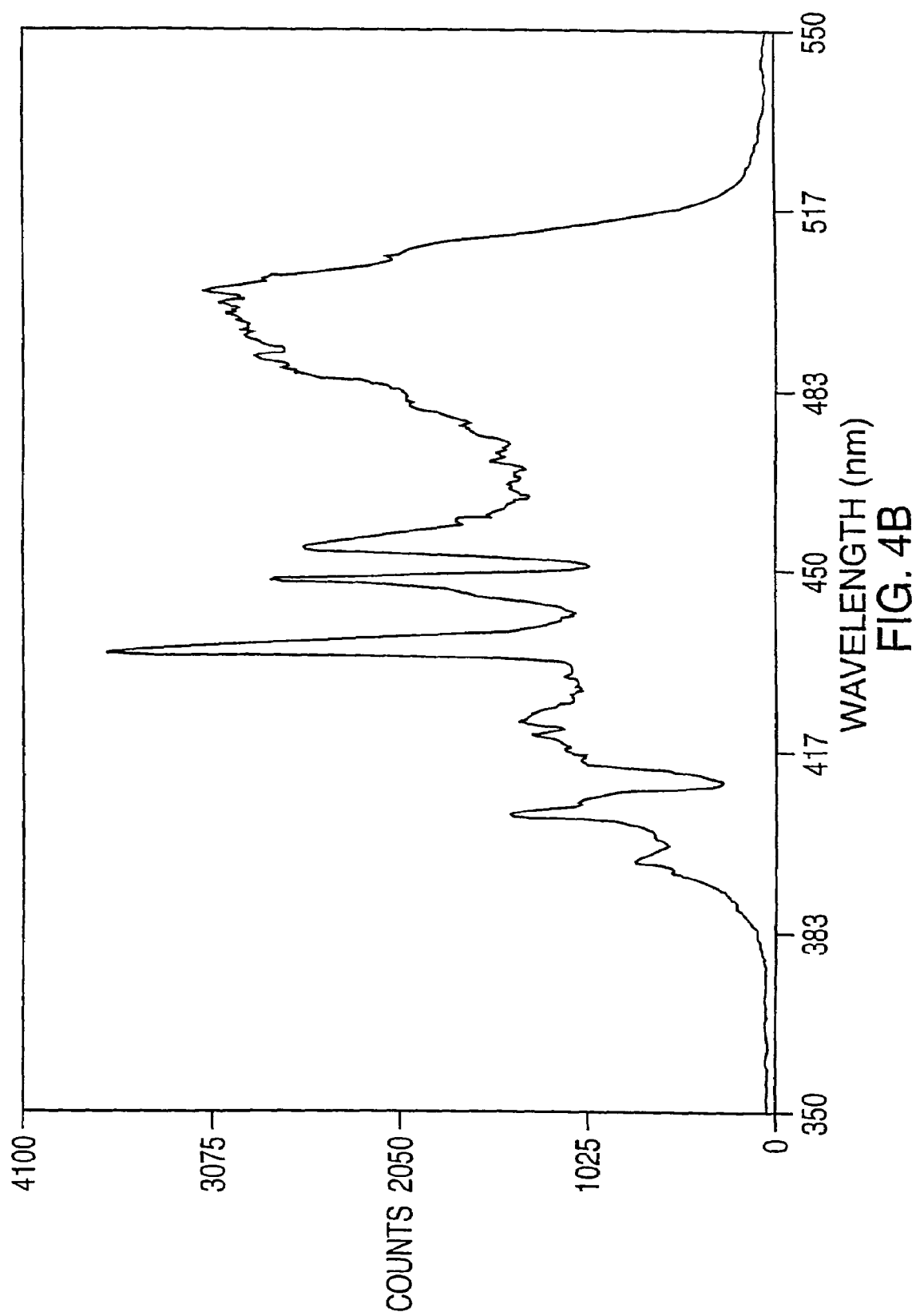
Figure 4C:
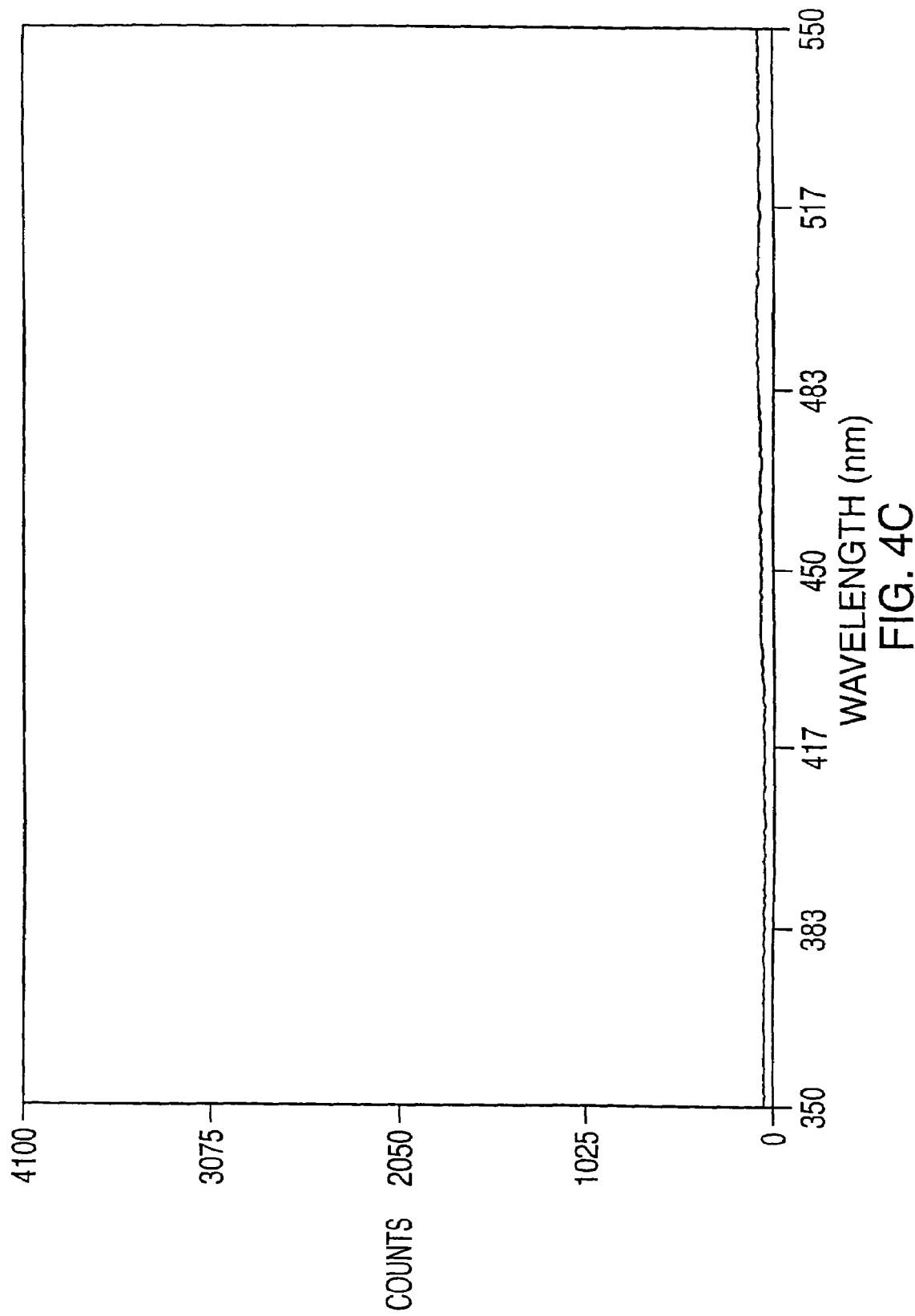
Figure 4D:
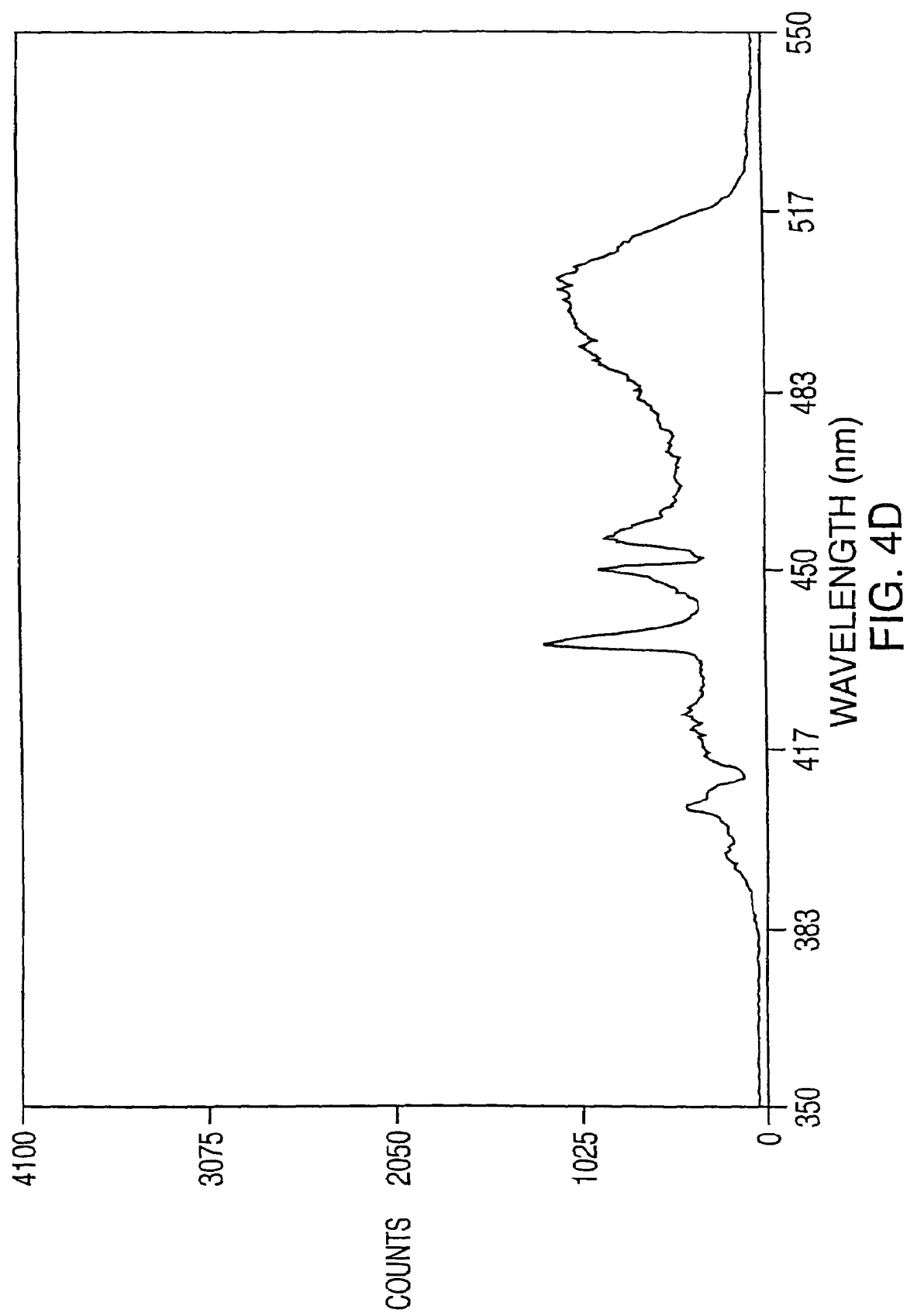
Figure 4E:
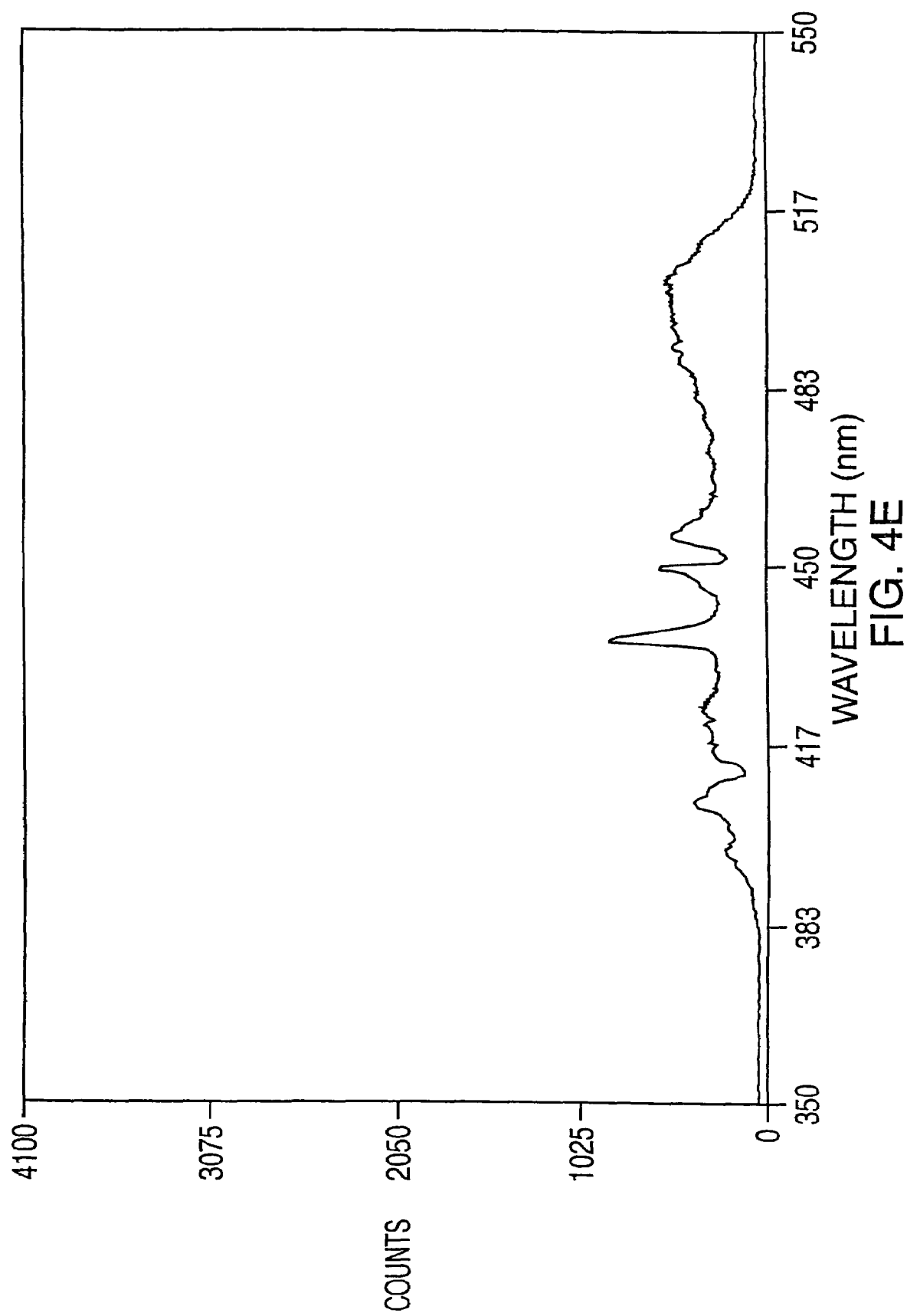

A comparative study of light transmission through various light and/or heat activated tooth whitening gels was undertaken. Spectral energy curves were generated using an Ocean Optics spectrometer with a 50 micron fiber for gather emission data. Light transmission through a glass microscope slide was used as a control and the test consisted of coating the slide with a 1-2 mm thick layer of each tooth whitening gel and illuminating with a metal halide light source connected to an 8 mm glass fiber optic light guide. The light was filtered through a 505 nm short pass filter (only wavelengths less than 505 nm pass through) prior to entering the light guide. The spectrometer's fiber optic probe was placed against the opposite side of the slide from the gel in order to detect the wavelengths of light allowed to pass through the gel on the slide. The spectral curves of FIGS. 4A-E clearly demonstrate the degree of light attenuation caused by all of the commercially available compositions. The spectral curves of FIGS. 4A-E clearly demonstrate the degree of light attenuation caused by all of the commercially available compositions: FIG. 4A—Control; FIG. 4B—Inventive Example I; FIG. 4C—Shofu Hi-Lite; FIG. 4D—QuasarBrite; Figure E—Opalescence Xtra.

The attenuation of power density, measured in $mW/cm^2$, was determined for the same four compositions by again placing a 1-2 mm layer of each gel or paste on a glass microscope slide and placing the slide/gel assembly in the path between the light source and the detector well of the power density meter. Due to the depth and shape of the detector well, the slide was 7 mm above the actual detector surface, rather than directly in contact with it. The power density was recorded at the beginning (B) and at the end of a 60 minute light exposure (E). The power density without slide or gel in the light path was adjusted to 175 $mW/cm^2$. The results are shown in Table 2 below.

TABLE 2

| Composition | U.S. Pat. No. | Energy Density ($mW/cm^2$) |
| --- | --- | --- |
| Control (slide only) | — | 165 |
| Example I (B) + (E) | — | 160 |
| & So Shofu Hi-Lite (B) | 5,032,178 | 25 |
| Shofu Hi-Lite (E) | 5,032,178 | 50 |
| QuasarBrite (B) | 5,240,415 | 110 |
| QuasarBrite (E) | 5,249,415 | 111 |
| Opalescence Xtra (B) | 5,785,527 | 65 |
| Opalescence Xtra (E) | 5,785,527 | 94 |

EXAMPLE III

Another transparent hydrogen peroxide gel was prepared that had a lower concentration of oxidizer (3% by weight of $H_2O_2$), but at a pH of 7.0 and a much higher viscosity (approximately 1,000,000 cps). The gel below was prepared in accordance with the procedure in Example I, except that a Kynar coated Ross Double Planetary vacuum mixer (Charles Ross & Sons, Haupaugge, N.Y.) was used to handle the elevated viscosity achieved during and after neutralization with the ammonium hydroxide. Sodium stannate was added as an additional stabilizer for the hydrogen peroxide.

| Ingredient | Percentage |
| --- | --- |
| Distilled water | 81.010 |
| Glycerin 99.7% | 5.000 |
| 1-hydroxyethylidene-1,1-diphosphonic acid | 0.400 |
| Sodium stannate | 0.015 |
| Hydrogen peroxide 35% | 8.570 |
| Carbopol 974P | 5.000 |
| Ammonium hydroxide 29% | to pH 7.0 |
| TOTAL | 100.000 |

The ability of the 3% hydrogen peroxide gel, transparent to visible light between the wavelengths of 380 and 700 nanometers, is demonstrated in Table 3 below.

TABLE 3

| Bovine Tooth # | Oxidizing Gel | Time Period | Light Source | Wavelength Range (nanometers) | Pulses/ Period | Power Density (mW/cm2) | Energy/ Pulse (Joules) | Delta E* |
| --- | --- | --- | --- | --- | --- | --- | --- | --- |
| B388 | Example II | 5 min | AR | 380-505 | 15 | | 4.84 | 19.67 |
| B388 | Example II | 5 min | AR | 380-505 | 15 | | 4.84 | 29.43 |
| B388 | Example II | 5 min | AR | 380-505 | 15 | | 4.84 | 32.74 |
| B365 | Example II | 5 min | None | — | 0 | | 0 | 3.41 |
| B365 | Example II | 5 min | None | — | 0 | | 0 | 4.23 |
| B365 | Example II | 5 min | None | — | 0 | | 0 | 5.78 |
| B365 | Example II | 5 min | AR | 380-505 | 15 | | 4.84 | 23.49 |
| B365 | Example II | 5 min | AR | 380-505 | 15 | | 4.84 | 30.27 |
| B367 | Example I | 30 min | TH | 400-520 | Continuous | 250 | | 32.26 |

*Elimination of positive Δa and Δb values from calculation.

EXAMPLE IV

Extracted human teeth (HE) that were non-carious and free of amalgam or resin-based restorative materials were utilized to study the ability of the inventive compositions to eliminate the stains from human enamel and dentin. The teeth were coated with a 1-2 mm thick film of an oxidizing gel and irradiated according to the regimens shown in Table IV below. The resulting change in tooth color (ΔShades) was recorded as the number of VITA® shade difference between the original baseline VITA® shade value and the final VITA® shade value.

TABLE 4

| Tooth # | Gel | Light Source | Exposure Time (min) | Pulses/Minute | Joules/Pulse | Shade (Initial) | Shade (Final) | Δ Shade: |
|---|---|---|---|---|---|---|---|---|
| HE2 | Example I | AR | 30 | 1 | 4.84 | B4 | C2 | 6 |
| HE3 | Example I | AR | 30 | 1 | 4.84 | A4 | A3.5 | 3 |
| HE4 | Example I | AR | 30 | 1 | 4.84 | A3 | B2 | 6 |
| HE5 | Example I | AR | 30 | 1 | 4.84 | B3 | D4 | 3 |
| HE6 | Example I | AR | 30 | 1 | 4.84 | B3 | B2 | 8 |
| HE7 | Example I | AR | 30 | 1 | 4.84 | A3 | A1 | 7 |
| HE8 | Example I | AR | 30 | 1 | 4.84 | A3.5 | A2 | 7 |
| HE9 | Example I | AR | 30 | 1 | 4.84 | A3 | A1 | 7 |
| HE10 | Example I | AR | 30 | 1 | 4.84 | A4 | A3.5 | 6 |
| HE11 | Example I | AR | 30 | 1 | 4.84 | A3.5 | A2 | 7 |
| HE12 | Example I | AR | 30 | 2 | 4.84 | A3.5 | A2 | 7 |
| HE13 | Example I | AR | 30 | 2 | 4.84 | B3 | B2 | 8 |
| HE14 | Example I | AR | 30 | 2 | 4.84 | A3.5 | B2 | 9 |
| HE15 | Example I | AR | 30 | 2 | 4.84 | A4 | A1 | 13 |
| HE16 | Example I | AR | 30 | 2 | 4.84 | B4 | B1 | 12 |
| HE17 | Example I | AR | 30 | 1 | 1.64 | A3 | A2 | 4 |
| HE18 | Example I | AR | 30 | 1 | 1.64 | B4 | B2 | 10 |
| HE19 | Example I | AR | 30 | 1 | 1.64 | C4 | D3 | 6 |
| HE20 | Example I | AR | 30 | 1 | 1.64 | B3 | A2 | 6 |
| HE21 | Example I | AR | 30 | 1 | 1.64 | B3 | B2 | 8 |
| HE22 | Example I | No light | 30 | 0 | 0 | B3 | A2 | 2 |
| HE23 | Example I | No light | 30 | 0 | 0 | A3 | A2 | 4 |
| HE24 | Example I | No light | 30 | 0 | 0 | B3 | D4 | 3 |
| HE25 | Example I | No light | 30 | 0 | 0 | D3 | B2 | 7 |
| HE26 | Example I | No light | 30 | 0 | 0 | B3 | A2 | 6 |
| HE27 | Example I | Tungsten Halogen | 60 | Continuous | 250 mW/cm2 | B3 | A1 | 9 |

EXAMPLE V

Human extracted teeth were whitened as follows by applying a 1-2 mm thick film of gel on the enamel surface and exposing the same surface to varying power densities from a metal halide light source with a 505 nm short pass internal filter. Comparisons were done to two controls, one of which was Gel exposure only (no light) and light exposure only (no Gel). Exposure regimens, consisting of gel application (except in the case of light only/no Gel), followed by 20 minutes of continuous light exposure, were repeated three times (3×20 minutes).

TABLE 5

| Tooth # | Gel | Light Source | Power Density (mW/cm2) | Filter | Test Duration | Initial Shade | Final Shade | Shade Change |
|---|---|---|---|---|---|---|---|---|
| HE101 | Example I | MH | 250 | 505 | 3 × 20 min | A3.5 | A1 | 7 |
| HE102 | Example I | MH | 250 | 505 | 3 × 20 min | B4 | A2 | 8 |
| HE103 | Example I | MH | 175 | 505 | 3 × 20 min | A3 | B1+ | 8 |
| HE104 | Example I | MH | 175 | 505 | 3 × 20 min | A4 | B2 | 12 |
| HE105 | Example I | MH | 175 | 505 | 3 × 20 min | B3 | B2 | 8 |
| HE106 | Example I | MH | 175 | 505 | 3 × 20 min | A3 | B1+ | 8 |
| HE107 | Example I | MH | 175 | 505 | 3 × 20 min | A4 | A2 | 10 |
| HE108 | Example I | No light | | | 3 × 20 min | A3.5 | A3 | 3 |
| HE109 | Example I | No light | | | 3 × 20 min | A4 | D3 | 5 |
| HE110 | Example I | No light | | | 3 × 20 min | A3.5 | A3.5 | 0 |
| HE111 | Example I | No light | | | 3 × 20 min | A4 | A3 | 6 |
| HE112 | Example I | No light | | | 3 × 20 min | A4 | A3.5 | 3 |
| HE113 | None | MH | 175 | 505 | 3 × 20 min | A3 | A3 | 0 |
| HE114 | None | MH | 175 | 505 | 3 × 20 min | A4 | A4 | 0 |
| HE115 | None | MH | 175 | 505 | 3 × 20 min | A3.5 | A3 | 3 |
| HE116 | None | MH | 175 | 505 | 3 × 20 min | B3 | B3 | 0 |

EXAMPLE VI

A pulpal chamber of an endo-tooth in a cooperative and informed patient was wired using a thermal probe and thermo-conducting paste. Pulpal temperatures were measuring during an actual whitening procedure, in which the illumination was supplied using the currently available Union Broach Illuminator and the device described in the instant application used at the most preferred wavelengths of 400 to 505 nanometers. Measurements of the energy densities at the tooth surface showed comparable energy densities for each device (230 milliwatts/cm$^2$ for the Union Broach Illuminator and 200 milliwatts/cm$^2$ for the device described in the instant application, respectively). The results are shown below in Table 6.

Illumination using the device described in the instant application in the preferred wavelength range from about 400 to 505 nanometers raised pulpal chamber temperature less than did the Union Broach device. In this experiment, temperatures rose to a maximum by twenty minutes and were then stable. In contrast to the temperature rise seen with the Union Broach device, at no time did the temperature using the device disclosed in the instant application rise above the 5.5° C. which could result in thermally induced pulpitis if maintained for a significant period of time. The temperature changes seen are likely to be greater than those seen with vital teeth as endo-teeth have no blood supply to provide additional cooling.

| Time | Temperature Rise (deg. C. from ambient) | |
| --- | --- | --- |
| (min.) | Union Broach | BriteSmile 2000 |
| 5 | 4 | 2.9 |
| 10 | 8 | 4.5 |
| 15 | 9 | 5.3 |
| 20 | 9 | 4.2 |
| 25 | 9.5 | 4.5 |
| 30 | 9 | 4.3 |

EXAMPLE VII

In order to determine the ability of the inventive apparatus described in FIGS. 6-20 to catalyze a light-activated tooth whitening gel and eliminate tooth stain, an in vitro study on stained bovine enamel was performed. Stained bovine enamel slabs were obtained that had been prepared as described in Example I above.

Enamel surface reflectance measurements over the entire visible spectrum were obtained using the CIELAB color scale (Commission International de L'Eclairage, Recommendations on uniform color spaces, color difference equations, and psychometric color terms, Supplement 2 to CIE publication 15 (E-13.1) 1971 (TC-1.3), 1978, Paris: Beaurea Central de la CIE, 1978). The CIELAB color scale evaluates color in terms of three axes of a color sphere, called L, a, and b. The "L" value is the axis in the color sphere which relates lightness and darkness on a scale from 0 (black) to 100 (white). The "a" value is the axis which relates color on a yellow to blue scale, with a 0 value in the center of the sphere, positive values toward the yellow, and negative values toward the blue. The "b" value is the axis which relates color on a red to green scale, with a 0 value in the center of the sphere, positive values toward the red, and negative values toward the green.

The stained enamel specimens were allowed to air-dry at room temperature 60 seconds before reflectance measurements were made. Measurements were conducted by aligning the center of a 4-mm square segment of stained enamel directly over the 3-mm aperture of the Minolta 503i reflectance spectrophotometer. An average of 5 reflectance readings using the L*a*b* factors were taken for each specimen.

The difference between the pre-treatment (baseline) and post-treatment readings for each color factor (L*, a*, and b*) represented the ability of the inventive LED array apparatus, in conjunction with the light-activated tooth whitening gel composition described below, to eliminate chromogens from the stained bovine teeth.

The overall change in color of stained pellicle was calculated using the CIELAB equation $$\Delta E = [(\Delta L^*)^2 + (\Delta a^*)^2 + (\Delta b^*)^2]^{1/2}$$

A "Corrected ΔE" value was calculated by eliminating from the above formulation the contribution of any positive Δa or Δb values (positive Δa and Δb values are changes in tooth color in the opposite direction from zero, and hence construed to add color, rather than remove it).

The light-activated tooth whitening composition used in conjunction with the inventive apparatus contained approximately 15% by weight hydrogen peroxide and 0.30 percent by weight of the photosensitizer precursor 1-hydroxyethylidene-1,1-diphosphonic acid (Dequest 2010, Monsanto Corp., St. Louis, Mo.). Highly purified water (18.2 megaohm, filtered through a 0.2 micron filter) was utilized in order to maintain good stability of the composition during storage. An additional stabilizer, potassium stannate, was also present in the mixture at a concentration of 0.02% by weight. The composition was thickened with a carboxypolymethylene polymer (Carbopol 974P, B.F. Goodrich Co., Cleveland, Ohio) to the consistency of a light, non-runny gel. Glycerin was added in a small percentage as a humectant and stabilizer (as a free radical scavenger), and the Carbopol 974P was neutralized to a pH of 6.50 with ammonium hydroxide, resulting in the formation of a transparent and thixotropic gel.

TABLE 6

| Ingredient | Percentage |
| --- | --- |
| Distilled water | 75.830 |
| 1-hydroxyethylidene-1,1-diphosphonic acid | 0.300 |
| Potassium stannate | 0.020 |
| Glycerin | 5.000 |
| Hydrogen peroxide | 15.000 |
| Carbopol 974P | 1.700 |
| Ammonium hydroxide 29% (add until pH = 6.5) | 2.150 |
| TOTAL | 100.000 |

The above composition was prepared initially in a plastic mixing chamber by combining, under agitation with a Teflon-coated mixing paddle the distilled water, the 1-hydroxyethylidene-1,1-diphosphonic acid, the potassium stannate, and the glycerin until a homogeneous slurry was obtained. The Carbopol 974P was then sifted slowly into the vortex created by the mixing paddle and allowed to mix until a homogeneous slurry of the polymer was obtained. Finally, the ammonium hydroxide was added in a constant, dropwise fashion over a period of about 5 minutes until thickening and clarification of the slurry occurred. A pH probe was inserted periodically and the ammonium hydroxide addition proceeded until a pH of exactly 6.50 was obtained. The resulting gel contained 15% by weight hydrogen peroxide, was highly transparent and had a thixotropic rheological properties (was non-slumping on a vertical surface). The viscosity of the resulting gel was 450,000 centipoise, as measured with a Brookfield RVT viscometer at 25 degrees C., spindle #5, and 0.5 rpm.

Each of 10 stained bovine enamel slabs was coated with a 1-2 mm thick film of the composition above for 20 minute periods and exposed during that time to actinic radiation from the inventive LED array apparatus. Table 7 below shows the results obtained by exposing gel-treated bovine enamel slabs to the LED array apparatus at a distance of approximately 1.75 inches from the surface of the array. This distance corresponded to a power density of approximately 130 mW/cm$^2$, which was confirmed using an Ophir Nova power meter connected to a 30A-SH thermopile detector. A separate group of 10 bovine enamel slabs was also coated with a 1-2 mm thick film of the same composition, but in this case not exposed to light in order to demonstrate the effect of the light in catalyzing the stain removing ability of the gel. Those results are also listed in Table 7 below.

TABLE 7

| Bovine Tooth # | Light | Total Gel Contact Time (minutes) | Power Density (mW/cm$^2$) | Delta E | Corrected Delta E* |
|---|---|---|---|---|---|
| B361 | NO | 20 | 0 | 22.24 | 22.24 |
| B311 | NO | 20 | 0 | 23.03 | 23.03 |
| B354 | NO | 20 | 0 | 17.01 | 16.97 |
| B147 | NO | 20 | 0 | 27.33 | 27.33 |
| B85 | NO | 20 | 0 | 19.24 | 18.99 |
| B211 | NO | 20 | 0 | 15.96 | 15.54 |
| B419 | NO | 20 | 0 | 17.79 | 15.97 |
| B249 | NO | 20 | 0 | 23.66 | 23.14 |
| B345 | NO | 20 | 0 | 21.10 | 21.10 |
| B114 | NO | 20 | 0 | 18.72 | 18.72 |
|  |  |  |  |  | AVG = 20.30 |
|  |  |  |  |  | SD = 3.74 |
| B248 | YES | 20 | 130 | 37.62 | 37.62 |
| B111 | YES | 20 | 130 | 43.20 | 43.20 |
| B283 | YES | 20 | 130 | 36.57 | 36.57 |
| B200 | YES | 20 | 130 | 36.92 | 36.92 |
| B420 | YES | 20 | 130 | 35.95 | 35.95 |
| B317 | YES | 20 | 130 | 36.13 | 36.13 |
| B399 | YES | 20 | 130 | 30.28 | 30.28 |
| B368 | YES | 20 | 130 | 34.06 | 34.06 |
| B270 | YES | 20 | 130 | 40.54 | 40.54 |
| B277 | YES | 20 | 130 | 37.19 | 37.19 |
|  |  |  |  |  | AVG = 36.85 |
|  |  |  |  |  | SD = 3.45 |

*Elimination of positive Δa and Δb values from calculation

The data in Table 1 demonstrates that:

(1) In the in vitro model described, exposure of bovine enamel slabs, contacted with the inventive gel composition above, to actinic radiation from an LED array light source resulted in significantly (p<0.001) reduced tooth stain as compared to slabs treated with just gel alone (and not exposed to the light source).

Upon reading the subject application, various alternative constructions and embodiments will become obvious to those skilled in the art. These variations are to be considered within the scope and spirit of the subject invention. The subject invention is only to be limited by the claims which follow and their equivalents.

What is claimed is:

1. A tooth illuminating apparatus comprising:
 a mouthpiece including a light source for projecting light energy onto the labial surfaces of plural teeth of a subject and at least one mouthpiece index disposed at a predetermined position relative to the light source, said at least one mouthpiece index comprises a dimple in a surface of said mouthpiece; and
 a positioner having at least one bite member adapted to be held by the subject between the subject's teeth and at least one locator disposed at a predetermined position relative to said at least one bite device, said positioner being adapted for attaching to said index;
wherein said positioner includes a spacer rod having an end connected to said bite member, said at least one locator comprising another end of said rod adapted to be received into said dimple.

2. The tooth illuminating apparatus of claim 1, wherein:
 said light source projects light from said mouthpiece in a predetermined pattern relative to the occlusal plane of the subject's teeth; and
 said positioner places said pattern in a predetermined spatial relationship with the subject's teeth when said at least one bite device is held between the subject's teeth.

3. The tooth illuminating apparatus of claim 1, wherein said mouthpiece further includes a mount for attaching said apparatus to a movable mounting arm.

4. The tooth illuminating apparatus of claim 3, wherein said light source projects a field of light with a substantially uniform light intensity onto the subject's teeth.

5. The tooth illuminating apparatus of claim 3, wherein said light source emits actinic light for activating a photosensitive composition applied to the subject's teeth.

6. The tooth illuminating apparatus of claim 5, wherein said actinic light has a wavelength in the range of about 350 nm to about 700 nm.

7. The tooth illuminating apparatus of claim 6, wherein said wavelength is within the range of about 400 nm to about 505 nm.

8. The tooth illuminating apparatus of claim 1, wherein said light source projects a field of light with a substantially uniform light intensity onto the subject's teeth.

9. The tooth illuminating apparatus of claim 1, wherein said light source emits actinic light for activating a photosensitive composition applied to the subject's teeth.

10. The tooth illuminating apparatus of claim 9, wherein said actinic light has a wavelength in the range of about 350 nm to about 700 nm.

11. The tooth illuminating apparatus of claim 10, wherein said wavelength is within the range of about 400 nm to about 505 nm.

12. The tooth illuminating apparatus of claim 1 further comprising at least one aperture disposed in a proximal portion of the mouth piece; and
 a passageway internal to said mouthpiece extending from said at least one aperture towards a distal portion.

13. The tooth illuminating apparatus of claim 12, wherein said passageway is for drawing air away from the teeth of the subject through said at least one aperture.

14. The tooth illuminating apparatus of claim 12 further comprising a fan for drawing cooling air through said mouthpiece.

15. The tooth illuminating apparatus of claim 14, wherein said fan is oriented to draw air from said passageway of said mouthpiece.

16. The tooth illumination apparatus of claim 12 wherein said light is pulsed, continuous, interrupted continuous or combinations thereof.

17. The tooth illuminating apparatus of claim 1 wherein said light energy is pulsed, continuous, interrupted continuous or combinations thereof.

18. The tooth illuminating apparatus of claim 1 further comprising at least one filter for limiting the wavelength of light emitted from the light source.

19. The tooth illumination apparatus of claim 1, wherein said light illuminates both upper and lower arches of said subject simultaneously.

* * * * *